United States Patent
Langhals et al.

(10) Patent No.: US 11,185,344 B2
(45) Date of Patent: Nov. 30, 2021

(54) TOOL FOR NEUROMA TREATMENT AND NERVE REGENERATION PROCEDURES

(71) Applicant: THE REGENTS OF THE UNIVERSITY OF MICHIGAN, Ann Arbor, MI (US)

(72) Inventors: Nicholas B. Langhals, Ypsilanti, MI (US); Cynthia Anne Chestek, Ann Arbor, MI (US); Paul S. Cederna, Milan, MI (US); Albert Shih, Ann Arbor, MI (US); Melanie G. Urbanchek, Fullerton, CA (US); Grant H. Kruger, Ypsilanti, MI (US); Jeffrey Stephen Plott, Algonac, MI (US); Jordan T. Kreda, Northville, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 751 days.

(21) Appl. No.: 15/556,893

(22) PCT Filed: Mar. 11, 2016

(86) PCT No.: PCT/US2016/021959
§ 371 (c)(1),
(2) Date: Sep. 8, 2017

(87) PCT Pub. No.: WO2016/149076
PCT Pub. Date: Sep. 22, 2016

(65) Prior Publication Data
US 2018/0042629 A1    Feb. 15, 2018

Related U.S. Application Data

(60) Provisional application No. 62/133,008, filed on Mar. 13, 2015.

(51) Int. Cl.
*A61B 17/295* (2006.01)
*A61B 17/3205* (2006.01)
(Continued)

(52) U.S. Cl.
CPC ............ *A61B 17/295* (2013.01); *A61B 17/29* (2013.01); *A61B 17/3205* (2013.01);
(Continued)

(58) Field of Classification Search
CPC ... A61B 17/295; A61B 17/3205; A61B 17/29; A61B 17/3417; A61B 17/3468;
(Continued)

(56) References Cited

U.S. PATENT DOCUMENTS 3,831,424 A * 8/1974 James ................... B21J 15/386
29/243.521
5,074,311 A 12/1991 Hasson
(Continued)

FOREIGN PATENT DOCUMENTS

WO    WO-2005110602 A1    11/2005

OTHER PUBLICATIONS

Grandi, P. De et al., "The morcellator knife: A new laparoscopic instrument for supracervical hysterectomy and morcellation," *Obstet. Gynecol.*, 95, 777-778 (May 2000).
(Continued)

*Primary Examiner* — Wade Miles
*Assistant Examiner* — Michael G Mendoza
(74) *Attorney, Agent, or Firm* — Harness, Dickey & Pierce, P.L.C.

(57) ABSTRACT

The present disclosure provides a mechanically-actuated tool for cutting a tissue graft having a hollow core and methods for use thereof. A portion of a biological structure, such as a nerve, is attached to the hollow core to form an implantable neural graft assembly. The tool has a cutter
(Continued)

mechanism and a grasper mechanism. The grasper mechanism has one or more component(s) that open and close via an actuation mechanism, like a handle, and rotate via a controller component, like a rotatable wheel. The cutter mechanism may be a cutting tube component that harvests the tissue graft. The tool may also have an ejector mechanism to remove the tissue graft as part of the implantable neural graft assembly. Such devices and methods are particularly suitable for treating neuromas and other neural regeneration procedures.

38 Claims, 17 Drawing Sheets

(51) Int. Cl.
    *A61B 17/34*     (2006.01)
    *A61B 17/29*     (2006.01)
    *A61B 17/11*     (2006.01)
    *A61B 90/00*     (2016.01)
    *A61B 17/00*     (2006.01)

(52) U.S. Cl.
    CPC .... *A61B 17/32053* (2013.01); *A61B 17/3417* (2013.01); *A61B 17/3468* (2013.01); *A61B 17/1128* (2013.01); *A61B 2017/00353* (2013.01); *A61B 2017/00438* (2013.01); *A61B 2017/00969* (2013.01); *A61B 2090/062* (2016.02)

(58) Field of Classification Search
    CPC .... A61B 17/32053; A61B 2017/00353; A61B 2017/00969; A61B 17/1128; A61B 2090/062
    See application file for complete search history.

(56) References Cited

U.S. PATENT DOCUMENTS

| | | | |
|---|---|---|---|
| 5,201,752 A * | 4/1993 | Brown | A61B 17/29 600/564 |
| 5,312,432 A | 5/1994 | Pingleton et al. | |
| 5,601,601 A | 2/1997 | Tal et al. | |
| 5,676,678 A * | 10/1997 | Schad | A61B 17/29 606/170 |
| 5,795,308 A | 8/1998 | Russin | |
| 5,807,378 A * | 9/1998 | Jensen | B25J 3/04 606/1 |
| 5,810,806 A * | 9/1998 | Ritchart | A61B 10/0266 604/21 |
| 5,820,009 A | 10/1998 | Melling et al. | |
| 6,139,508 A | 10/2000 | Simpson et al. | |
| 6,149,607 A | 11/2000 | Simpson et al. | |
| 6,234,177 B1 | 5/2001 | Barsch | |
| 6,270,472 B1 | 8/2001 | Antaki et al. | |
| 6,387,056 B1 | 5/2002 | Kieturakis | |
| 6,447,522 B2 | 9/2002 | Gambale et al. | |
| 6,558,359 B1 * | 5/2003 | Stiles | A61B 17/3468 604/164.06 |
| 7,087,071 B2 | 8/2006 | Nicholas et al. | |
| 7,488,296 B1 | 2/2009 | Van Andel | |
| 8,523,886 B2 | 9/2013 | Grigoryants et al. | |
| 2005/0049520 A1 | 3/2005 | Nakao | |
| 2005/0251187 A1 * | 11/2005 | Beane | A61B 17/0218 606/180 |
| 2006/0184198 A1 | 8/2006 | Bales et al. | |
| 2007/0239066 A1 | 10/2007 | Laham et al. | |
| 2008/0249502 A1 | 10/2008 | Thompson et al. | |
| 2008/0255597 A1 * | 10/2008 | Pravong | A61B 17/32002 606/169 |
| 2010/0137889 A1 | 6/2010 | Oren et al. | |
| 2010/0249700 A1 | 9/2010 | Spivey | |
| 2010/0256662 A1 | 10/2010 | Racenet et al. | |
| 2010/0292724 A1 | 11/2010 | Ravikumar et al. | |
| 2012/0010615 A1 * | 1/2012 | Cummings | A61B 18/1445 606/51 |
| 2012/0289860 A1 | 11/2012 | McClellan | |
| 2013/0144292 A1 | 6/2013 | To | |
| 2013/0304174 A1 | 11/2013 | Langhals et al. | |
| 2014/0005763 A1 | 1/2014 | Cederna et al. | |
| 2014/0378957 A1 | 12/2014 | Orphanos et al. | |
| 2016/0143751 A1 | 5/2016 | Chestek et al. | |

OTHER PUBLICATIONS

Lim, Jonas J.B. et al., "A review of mechanism used in laparoscopic surgical instruments," *Mechanism and Machine Theory*, 38, pp. 1133-1147 (2003); DOI:10.1016/S0094-114X(03)00063-6.

Mackinnon, Susan E. et al., "Alteration of Neuroma Formation by Manipulation of Its Microenvironment," *Plast. Reconstr. Surg.* 76, pp. 345-353 (Sep. 1985).

Matern, U. et al., "Ergonomic aspects of five different types of laparoscopic instrument handles under dynamic conditions with respect to specific laparoscopic tasks: An electromyographic-based study," *Surg. Endosc.*, 18, pp. 1231-1241 (2004); DOI: 10.1007/s00464-003-9162-1.

Moore, Jason Z. et al., "Blade Oblique Cutting of Tissue for Investigation of Biopsy Needle Insertion," *Trans. NAMRI*, 37, pp. 49-56 (2009).

Moore, Jason Z. et al., "Hollow needle tissue insertion force model," *CIRP Ann.—Manuf. Technol.* 60, pp. 157-160 (2011); doi:10.1016/j.cirp.2011.03.101.

Moore, Jason Z. et al., "Modeling of the Plane Needle Cutting Edge Rake and Inclination Angles for Biopsy," *J. Manuf. Sci. Eng.* 132, 051005 (Oct. 2010); DOI: 10.1115/1.4002190.

Moore, Jason Z. et al., "Novel needle cutting edge geometry for end-cut biopsy," *Med. Phys.* 39 (1), pp. 99-108 (Dec. 12, 2011); DOI: 10.1118/1.3665253.

Sakai, Yasuo et al., Prevention and Treatment of Amputation Neuroma by an Atelocollgen Tube in Rat Sciatic Nerves *J. Biomed. Mater. Res. B. Appl. Biomater.* 73, 355-360 (Mar. 25, 2005); DOI: 10.1002/jbm.b.30219.

Thomas, Michael et al., "Freeze-thawed Muscle Grafting for Painful Cutaneous Neuromas," *J. Bone Joint Surg. Br.*, 76, pp. 474-476 (1994).

Urbanchek, M. et al., "Electrophysiological Characteristics of Regenerative Peripheral Nerve Interface Bio-Devices," *ifess2012.com* 132, pp. 1515-1523 (2013).

Vaienti, Luca et al. "Perineural Fat Grafting in the Treatment of Painful Neuromas," *Tech Hand Surg.* 16 (1), pp. 52-55 (Mar. 2012).

Extended European Search Report and Written Opinion for European Application No. 16765484.7 dated Nov. 12, 2018, 7 pages.

International Search Report and Written Opinion for PCT/US2016/021959, dated Jun. 1, 2016; ISA/KR.

* cited by examiner

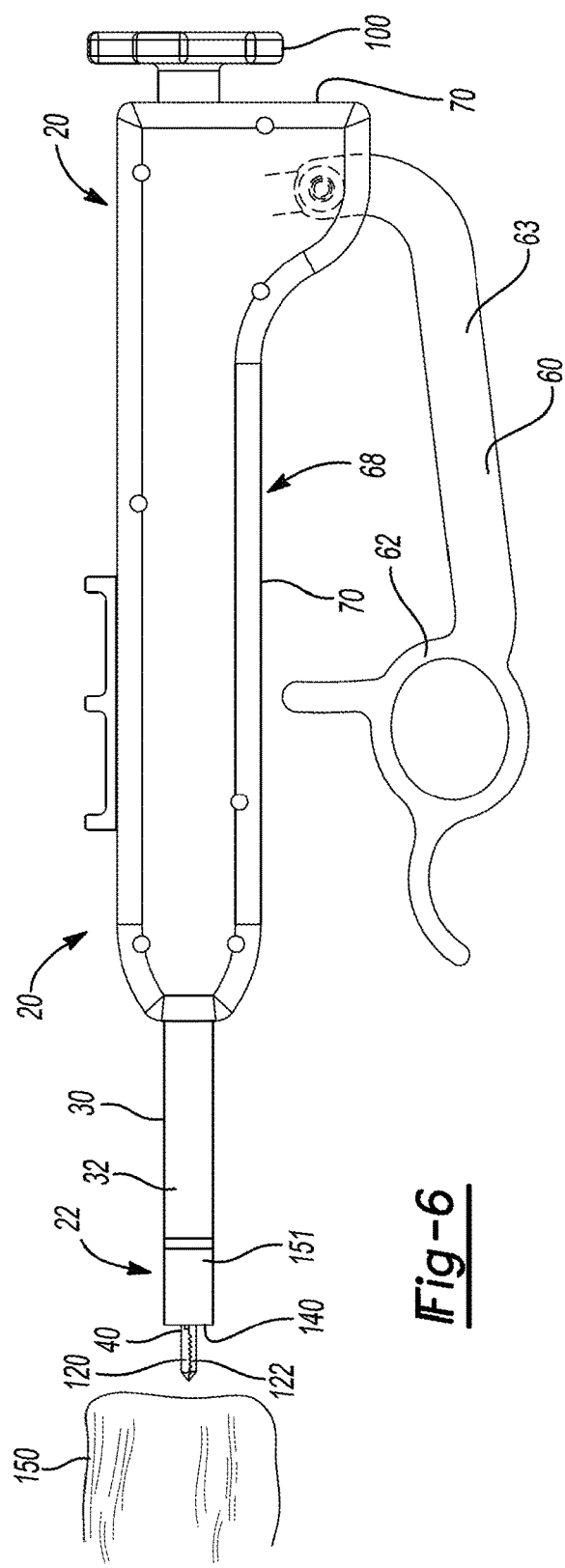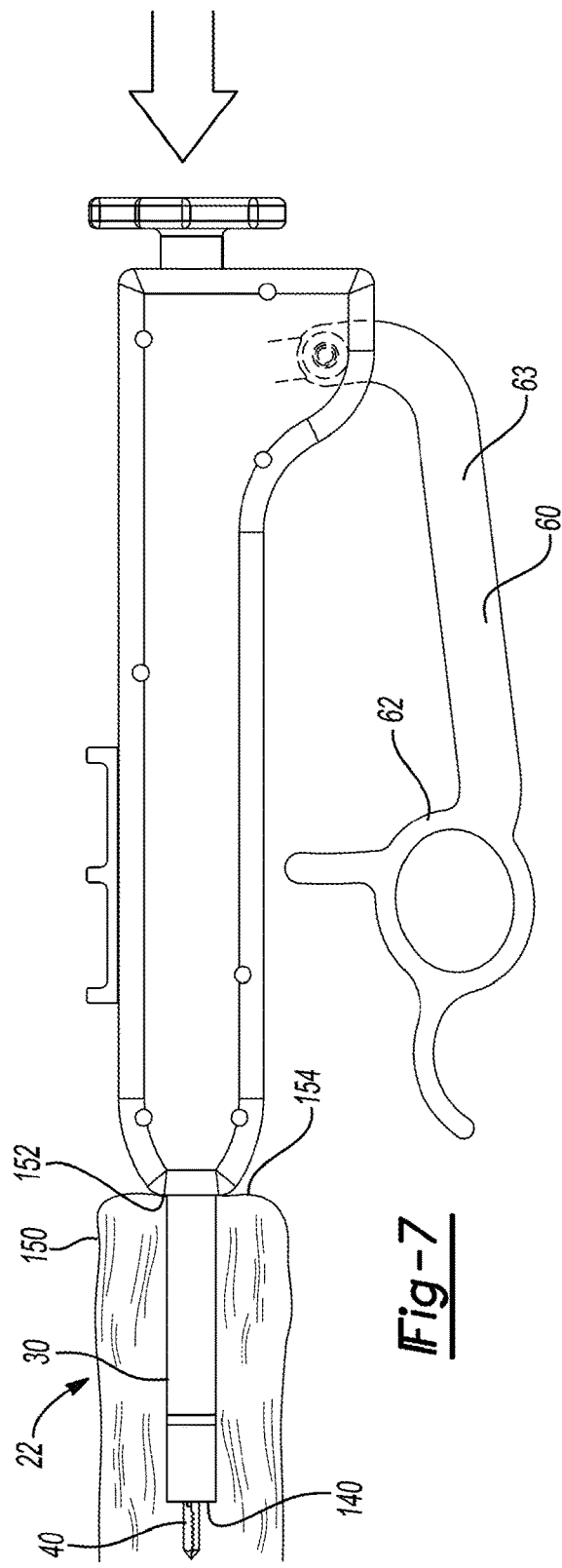

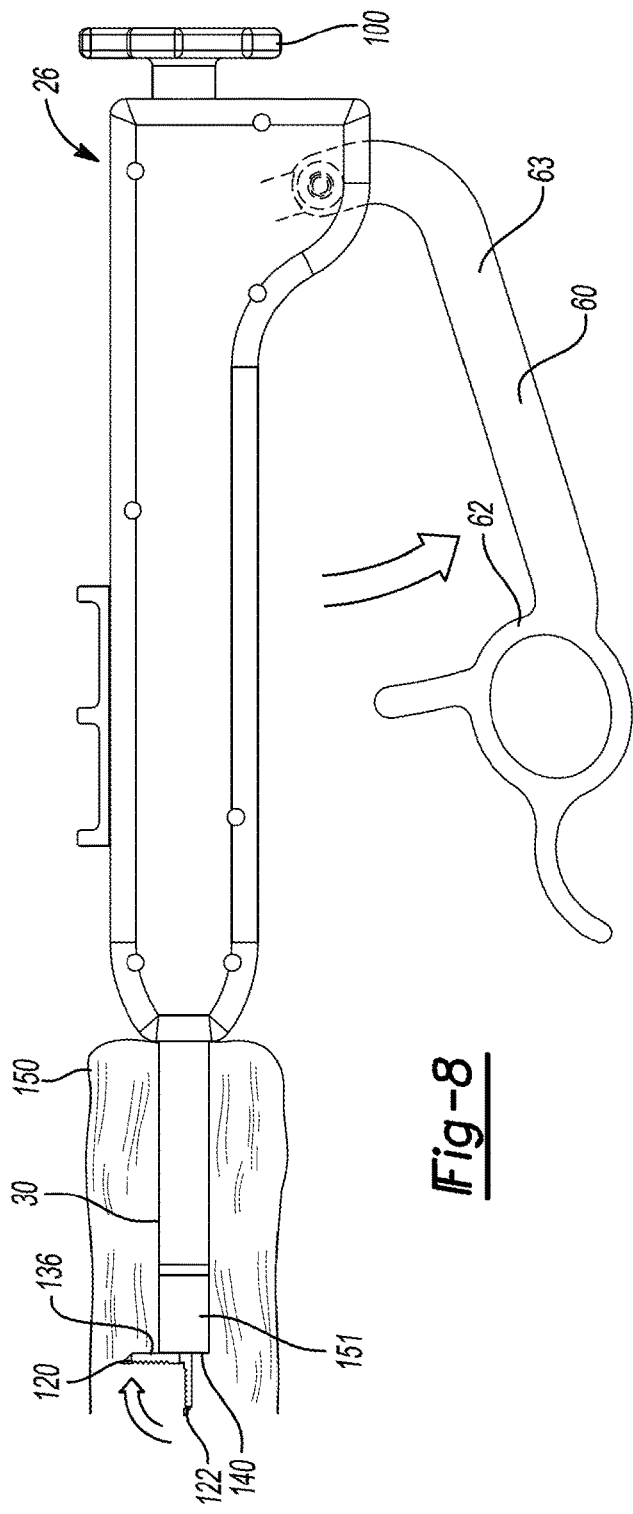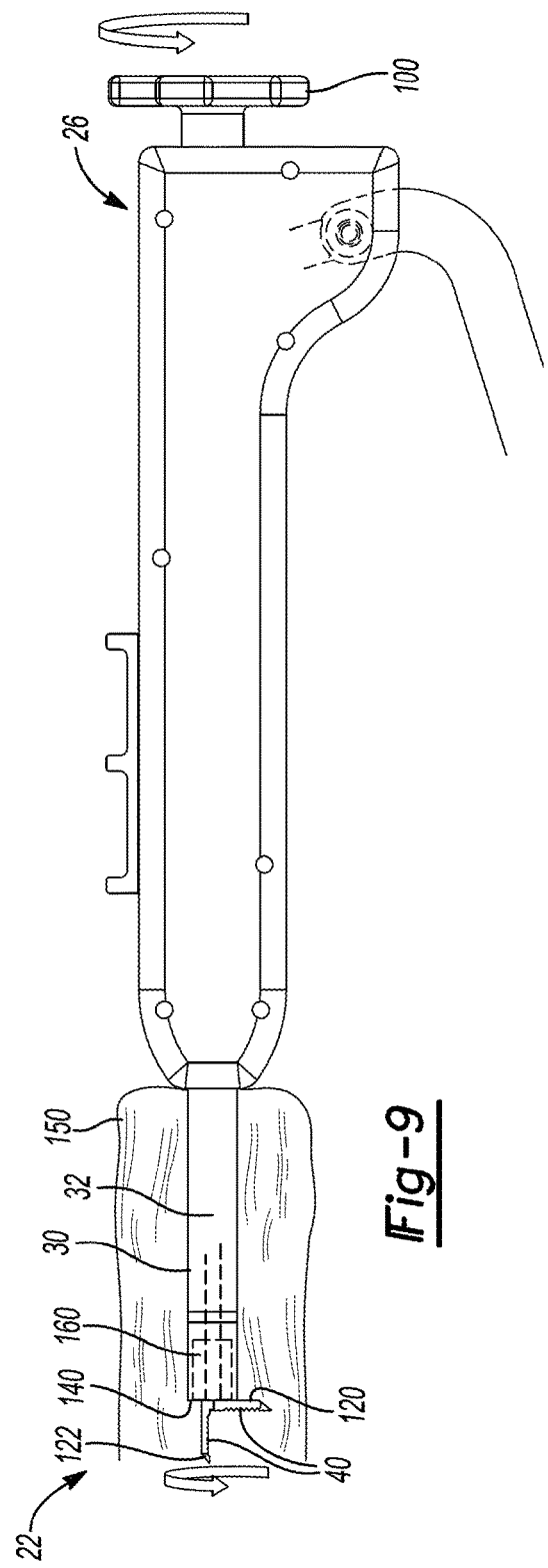

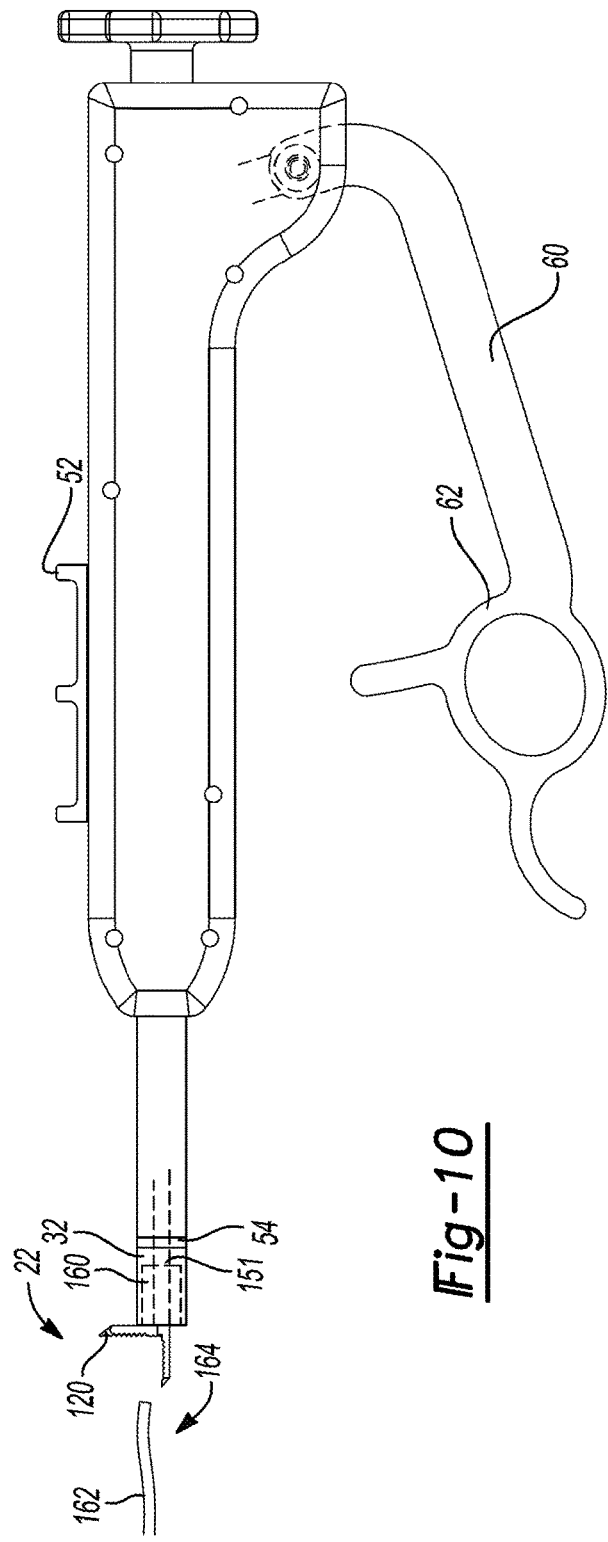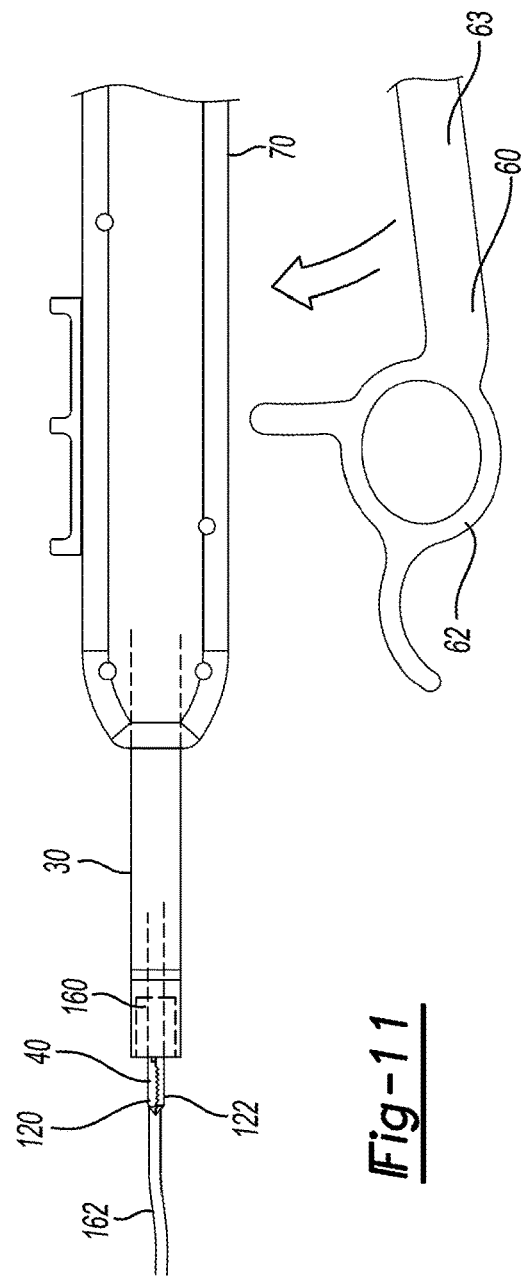
Fig-10
Fig-11

TOOL FOR NEUROMA TREATMENT AND NERVE REGENERATION PROCEDURES

CROSS-REFERENCE TO RELATED APPLICATIONS

This application is a U.S. National Phase Application under 35 U.S.C. 371 of International Application No. PCT/US2016/021959 filed on Mar. 11, 2016 and published as WO 2016/149076 A1 on Sep. 22, 2016. This application claims the benefit of U.S. Provisional Application No. 62/133,008, filed on Mar. 13, 2015. The entire disclosures of the above applications are incorporated herein by reference.

FIELD

The present disclosure relates to a medical device or tool and methods for use thereof to extract a tissue graft from a subject, and then implant and associate the tissue graft with a biological component, such as a nerve, in the subject. Such a tool can be used in neural surgical procedures, such as neuroma treatment or nerve regeneration surgical procedures.

INTRODUCTION

This section provides background information related to the present disclosure which is not necessarily prior art.

There is a need to create reliable and improved neural interfaces. Neural interfaces can be used to receive and record signals from nerves (for example, mammalian or human nerves) for subsequent processing and use in controlling prosthetic limbs, and/or in monitoring, diagnosing, and detecting conditions such as pathological pain signals, pathological contractions, tremor, spasticity, and the like, within an animal body and nervous system. For example, where a subject has an amputated limb, artificial limbs may be connected to the amputated limb via a neural interface. Such a neural interface may include an implanted electrode or wire that is in electrical communication with both neural tissue in the subject and with external componentry of the artificial limb.

Conventional neural interfaces initially may be capable of controlling prosthetic devices, but signal degradation and failure gradually occurs from scarring, inflammation, and axonal pruning. Further, because of the inherently small size of many nerve fibers, especially of peripheral nerves, a nerve with an implanted electrode can develop scar tissue, which can represent a substantial fraction of the nerve and cause significant signal interference. Further, even without scarring, the signals detected by current systems utilizing sufficiently small electrodes are typically less than 100 microvolts, peak-to-peak ($\mu V$ pp) when recording from within the nerve and less than 10 $\mu V$ pp when recording from a cuff around the nerve. At these low levels, the signals detected by current systems are subject to significant noise and interference and can require significant, extensive hardware resources and processing power for detection, processing, and analysis of such signals. Thus, methods and tools for creating improved neural interfaces having improved signals would be highly desirable.

Neural interfaces may also be used to treat or minimize neuroma formation where there is a traumatic injury, disease, or other long-term neural degradation. For example, after trauma occurs, divided or severed peripheral nerves can regenerate and sprout nerve fibers in search of new neural targets. When these new nerve fibers are not provided with any distal target for reinnervation, neuromas are formed, which are tiny disorganized clusters of these nerve fibers. The regenerating nerve fibers continue to sprout new branches from the proximal end of the divided nerve, causing a large mass of tangled motor and sensory axons, Schwann cells, endoneurial cells, perineurial cells, and a dense collagenous matrix with surrounding fibroblasts. Neuromas form in all patients who suffer loss of a limb; approximately 25% of these neuromas will become painful. In the nerve stumps of amputated limbs, this detrimental response at the proximal end of a divided peripheral nerve can be a source of pain for the patient, as well as a source of signal interference when decoding action potentials. The syndromes of painful neuroma include extreme spontaneous pain, hyperalgesia, pain to touch (allodynia), and cold intolerance. This unremitting pain adversely impacts a patient's quality of life, which can potentially lead to depression, insomnia, and functional impairment through prosthetic limb abandonment. Current surgical techniques for neuroma treatment or neural regeneration procedures are long, arduous, and require extensive skill of the surgeon.

Accordingly, there is a need for simplifying formation of neural interfaces that can be used for neuroma treatment or other neural regeneration procedures, such as making regenerative neuromuscular constructs (RNCs), by way of non-limiting example. It would be desirable to have a specialized medical device tool that can be used in an efficient, safe, and repeatable manner to form such improved neural interfaces within a subject or patient. Further, it would be desirable to have a specialized medical device tool that reduces associated time and skill required intraoperatively to conduct such procedures to form improved neural interface assemblies.

SUMMARY

This section provides a general summary of the disclosure, and is not a comprehensive disclosure of its full scope or all of its features.

In various aspects, the present disclosure provides a tool or device for creating an implantable neural graft assembly in a subject. In certain aspects, a device comprises a cutter mechanism for creating (e.g., cutting/excising and removing) a tissue graft having a hollow central region from a source of tissue in the subject. The cutter mechanism comprises one or more cutter components. The device also optionally comprises a grasper mechanism capable of retaining a nerve end of the subject in a first position and releasing the nerve end in a second position. The grasper mechanism comprises one or more grasper components. The device also includes an actuation mechanism that when activated is configured to dispose the tissue graft over the nerve end. The device thus creates the implantable neural graft assembly comprising the nerve end disposed within the free tissue graft.

In certain other aspects, a tool or device is provided for creating an implantable neural graft assembly. The device comprises a cutter mechanism having a cutting tube with an internal bore and a terminal end that excises a tissue graft from a source of tissue in the subject. The device also comprises a grasper mechanism comprising a plurality of grasper component members that move from a first closed position to a second open position. In the first closed position, the plurality of grasper component members is capable of retaining a nerve end. In the second open position, at least one of the grasper components has a cutting edge that cooperates with the terminal end of the cutting tube to create (e.g., cut or excise) a free tissue graft contained in the internal bore. A handle moves the plurality of grasper component members from the first closed position to the second open position. The plurality of grasper component members can be rotated to greater than or equal to about 360°, as well. The device further includes an actuation mechanism, such as an ejector assembly, which may include an ejector, capable of linearly translating in a portion of the internal bore of the cutting tube to eject the free tissue graft from the terminal end. The device thus creates the implantable neural graft assembly comprising the nerve end disposed within the free tissue graft.

In other aspects, the present disclosure provides a kit for creating an implantable neural graft assembly in a subject. The kit comprises a cutter component for cutting and removing a tissue graft from a source of tissue in the subject to form a cylindrical tissue graft. The kit also comprises a grasper component capable of retaining a nerve end of the subject within the cylindrical tissue graft. The kit further comprises at least one connector for affixing a portion of the nerve end within the cylindrical tissue graft for forming the implantable neural graft assembly comprising the nerve end disposed and affixed within the free tissue graft.

In yet other aspects, a method of forming an implantable neural graft assembly in a subject is provided by the present disclosure. The method comprises introducing a device comprising a cutter mechanism and a grasper mechanism into a source of tissue in the subject. Then, the method comprises cutting a free tissue graft from the source of tissue with the cutter mechanism, wherein the free tissue graft is retained in the cutter mechanism as the device is removed from the source of tissue. The method also comprises grasping a nerve end with the grasper mechanism and introducing it into a portion of the free tissue graft, followed by ejecting the free tissue graft from the device to create the implantable neural graft assembly comprising the nerve end disposed within the free tissue graft.

In certain other aspects, the present disclosure provides a method of forming an implantable neural graft assembly in a subject. The method optionally comprises cutting a tissue graft having a hollow core region from a source of tissue with a tool and retaining the tissue graft in the tool. Then, a biological structure is introduced into a portion of the hollow core region of the tissue graft with the tool to dispose the biological structure in the hollow core region of the tissue graft. The method also comprises ejecting the tissue graft and releasing the biological structure from the tool to create the implantable neural graft assembly comprising the biological structure and the tissue graft.

In other variations, the present disclosure provides a method of forming an implantable neural graft assembly in a subject. The method comprises introducing a device comprising a cutter mechanism, for example, comprising a cutter tube component, and a grasper mechanism, for example, comprising a plurality of grasper component members, into a source of tissue in the subject. Then, a free tissue graft is excised from the source of tissue. The free tissue graft is retained in the cutting tube as the device is removed from the source of tissue. Next, the method includes grasping a nerve end with the plurality of grasper component members, followed by ejecting the free tissue graft from the device over the nerve end to create the implantable neural graft assembly having the nerve end disposed within the free tissue graft.

In yet other variations, the present disclosure contemplates a method of forming an implantable neural graft assembly in a subject. The method comprises cutting a tissue graft having a hollow core from a source of tissue with a tool and retaining the tissue graft in the tool. Then, the tool introduces a biological structure into a portion of the hollow core of the tissue graft to dispose the biological structure within the hollow core of the tissue graft. Finally, the tissue graft and biological structure are ejected from the tool as an implantable assembly of the biological structure and the tissue graft.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a side view of a tool for creating a peripheral nerve interface in a subject in accordance with certain aspects of the present disclosure. The tool is being directed towards a source of tissue in a subject prior to extraction of a free tissue graft.

FIG. 7 is a side view of the tool in FIG. 6 where a terminal end of the tool, including a cutting tube and a plurality of grasper component members, has been introduced into tissue of a subject from which a free tissue graft or core will be removed (so that the inserted cutting tube has an open central region that contains tissue captured via the insertion process).

FIG. 8 is a side view of the tool in FIGS. 6-7, where a handle of the tool is moved into an open position, so that one of the plurality of grasper component members is deployed into an open, cutting position.

FIG. 9 is a side view of the tool in FIGS. 6-8, where a finger wheel of the tool is rotated so as to rotate one of the plurality of grasper component members having a cutting edge along a terminal edge of the cutting tube to cut and detach a tissue core disposed within a central region of the cutting tube.

FIG. 10 is a side view of the tool in FIGS. 6-9, where a tissue core has been extracted from the subject and is introduced into a surgical location of the subject having a peripheral nerve end.

FIG. 11 is a side view of the tool in FIGS. 6-10, where the peripheral nerve end is grasped by the plurality of grasper component members on the terminal end of the tool.

Figure 16:
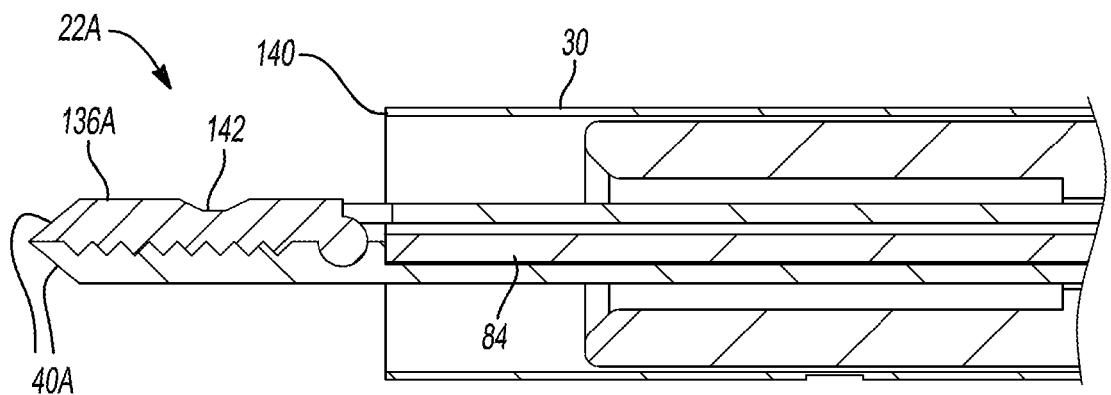

FIG. 16 is a detailed view of an alternative variation of a distal end of a device for creating a peripheral nerve interface in accordance with certain aspects of the present disclosure having a grasper mechanism including a plurality of grasper component members, where one of the grasper components has a recessed portion that permits a terminal end of a cutting tube of a cutting mechanism to seat therein, shown in a closed position.

Figure 17:
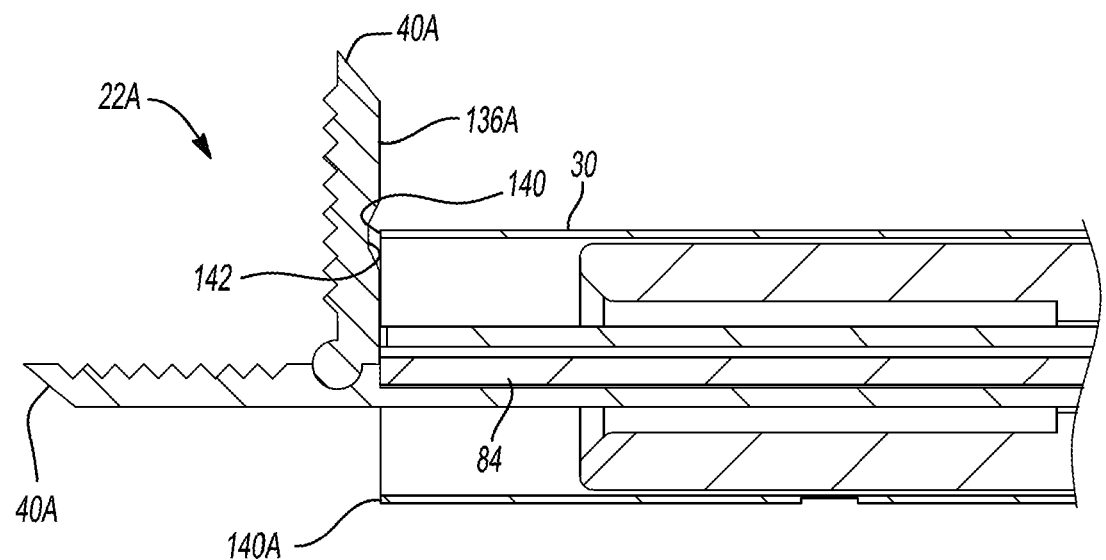

FIG. 17 is a detailed view of an alternative variation of a distal end of a device for creating a peripheral nerve interface in accordance with certain aspects of the present disclosure having a grasper mechanism including a plurality of grasper component members, where one of the grasper components has a recessed portion that permits a terminal end of a cutting tube of a cutting mechanism to seat therein, shown in an open position for cutting tissue.

Figure 18:
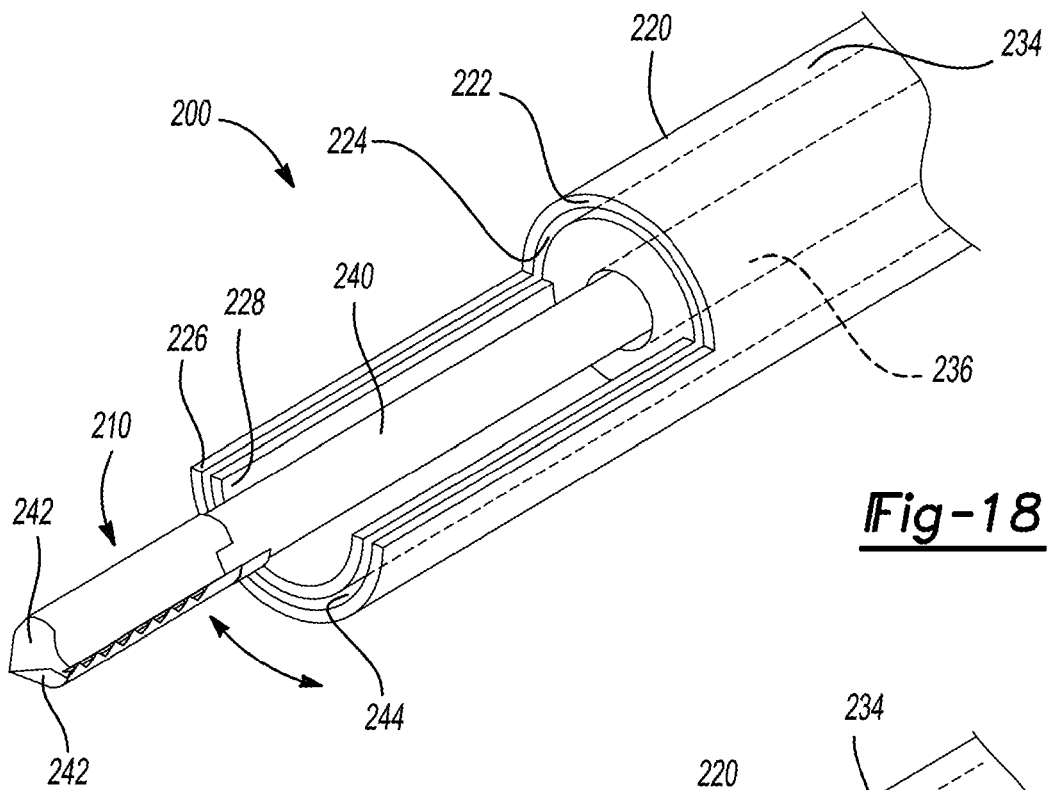

FIG. 18 is a perspective view of an alternative variation of a device or tool for creating a peripheral nerve graft interface or assembly in a subject in accordance with certain aspects of the present disclosure having a cutter mechanism including a cutting tube having two bifurcated portions along a terminal end that are concentrically arranged and aligned with one another to permit rotation of one of the bifurcated portions to cut and remove the tissue graft.

Figure 19:
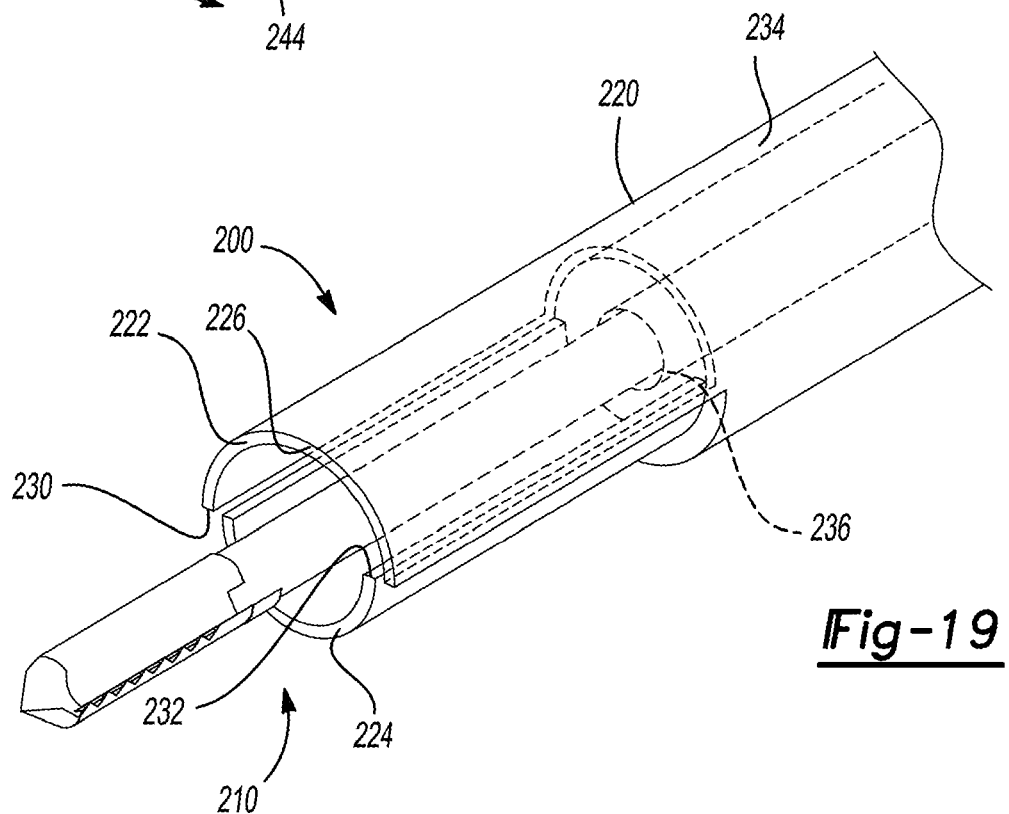

FIG. 19 is a perspective view of the device of FIG. 18, where a first bifurcated portion is rotated 180° with respect to a second bifurcated portion to permit cutting and removal of a cylindrical tissue graft having a hollow core.

Figure 20:
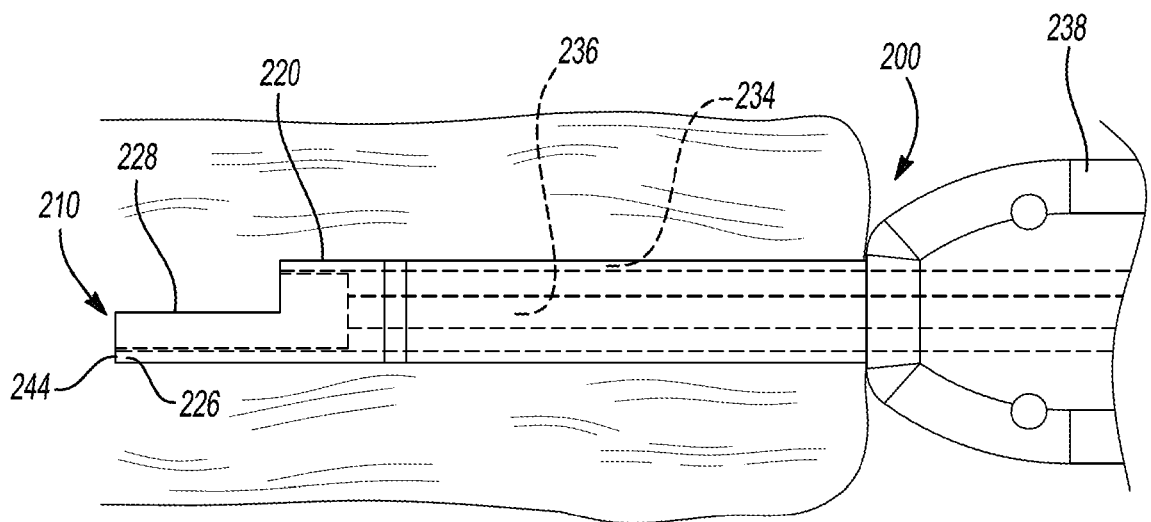

FIG. 20 is a side view of a tool shown in FIGS. 18-19 being used to create a peripheral nerve graft interface or assembly in a subject in accordance with certain aspects of the present disclosure. The tool is inserted into tissue of a subject from which a free tissue graft will be removed prior to extraction of the free tissue graft.

Figure 21:
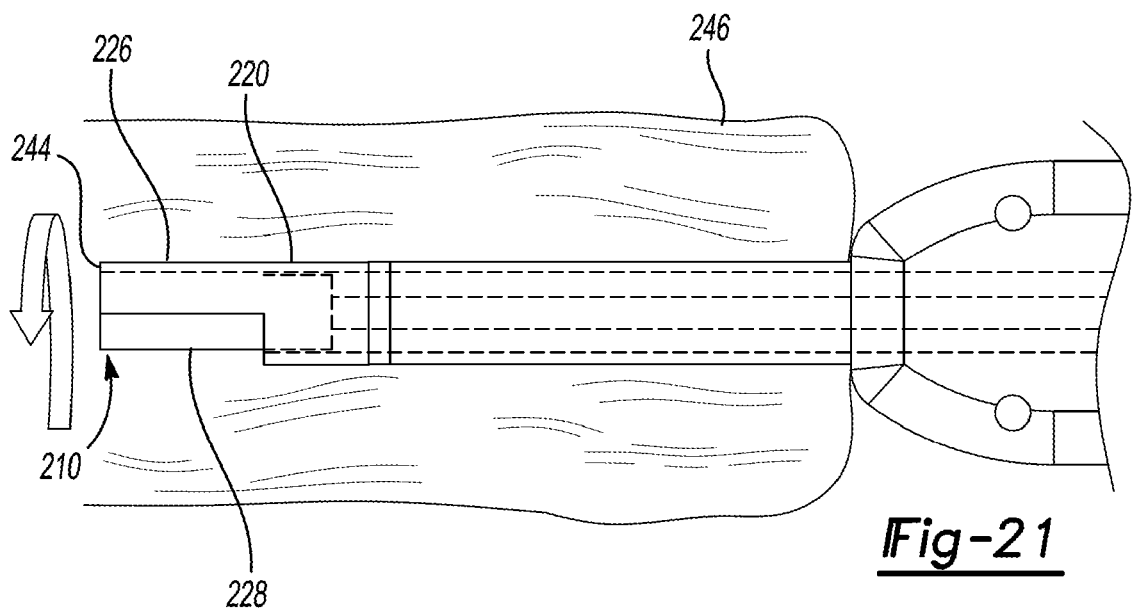

FIG. 21 is a side view of the tool shown in FIGS. 18-20, where a first bifurcated portion is rotated 180° with respect to a second bifurcated portion to permit cutting and removal of a cylindrical tissue graft having a hollow core (so that an inserted cutting tube has an open central region that contains tissue captured via the insertion and rotation process).

Figure 22:
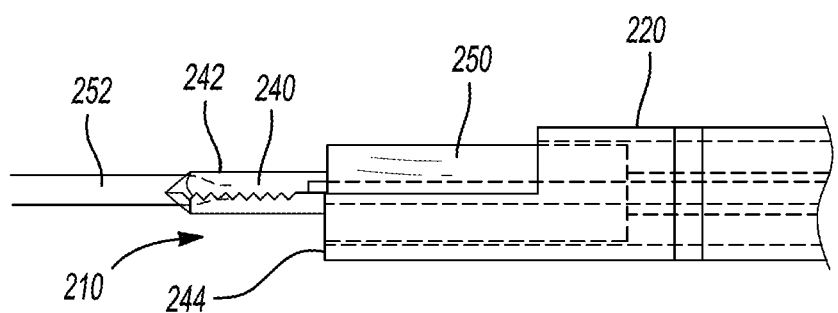

FIG. 22 is a side view of the tool in FIGS. 18-21, where a tissue graft has been extracted from the subject within the tool and is introduced into a surgical location of the subject having a peripheral nerve end, where the peripheral nerve end is grasped by a grasper mechanism in the form of a plurality of grasper component members on the terminal end of the tool.

Figure 23:
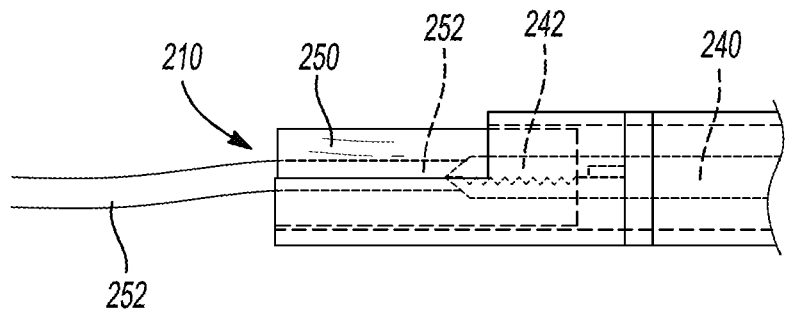

FIG. 23 is a side view of the tool in FIGS. 18-22, where the tissue graft is being ejected from the tool and thus disposed over the nerve end to form a nerve graft interface assembly.

Figure 24:
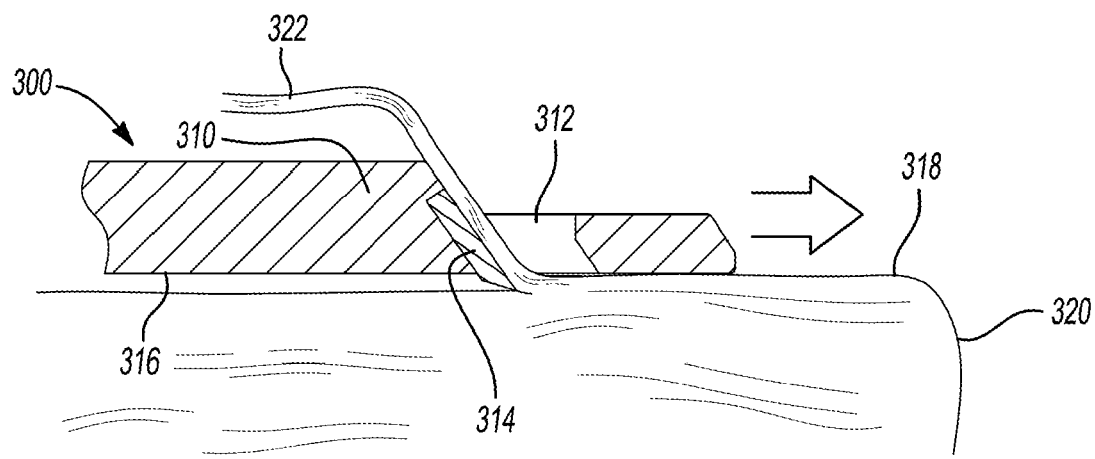

FIG. 24 is a side view of yet another variation of a device or tool for creating a peripheral nerve graft interface or assembly in a subject in accordance with certain aspects of the present disclosure having a cutter mechanism in the form of a box plane cutter (e.g., a mandolin style cutter) that harvests a planar free tissue graft from a source of tissue by being directed in a direction parallel to a surface of the tissue.

Figure 25:
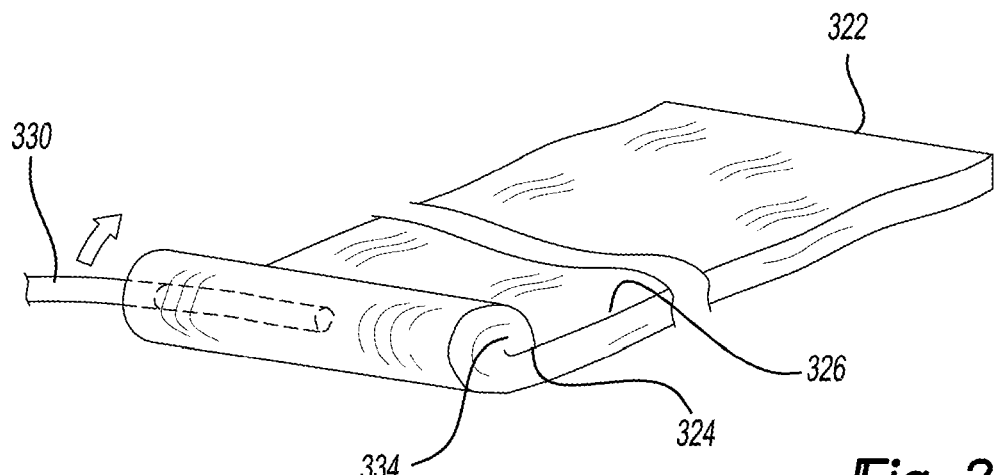

FIG. 25 shows the planar free tissue graft harvested from a box plane style cutter component in FIG. 24 having a nerve end disposed therein and being rolled to form a cylindrical nerve graft interface assembly.

Figure 26:
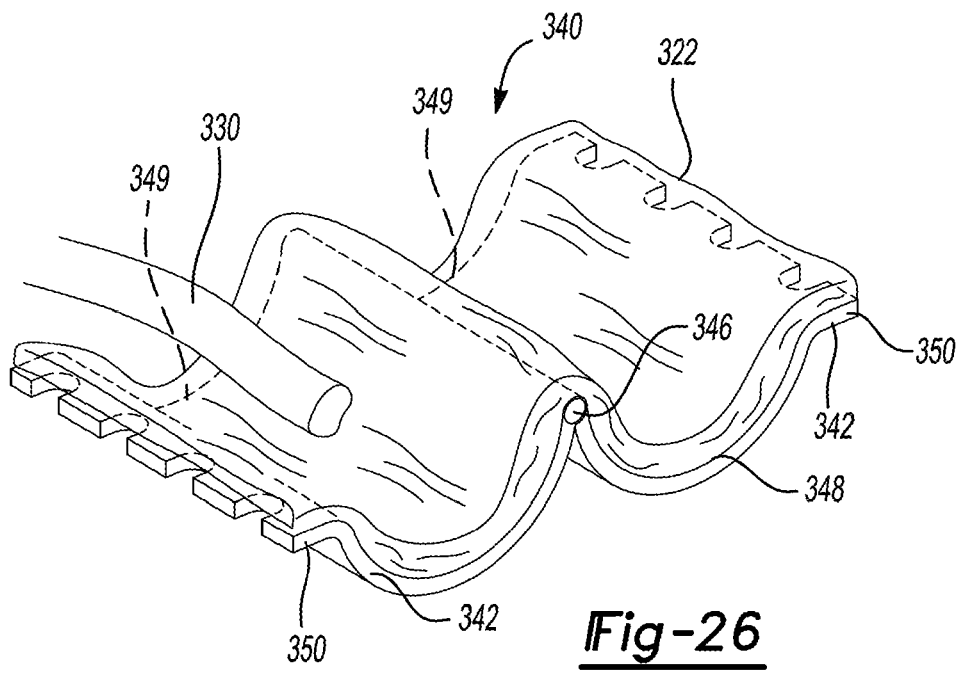

FIG. 26 shows an additional tool in the form of a clamshell templating device for creating a cylindrical tissue graft with a connector in accordance with certain aspects of the present disclosure, where the clamshell portions are open and a planar sheet of tissue graft is disposed therein.

Figure 27:
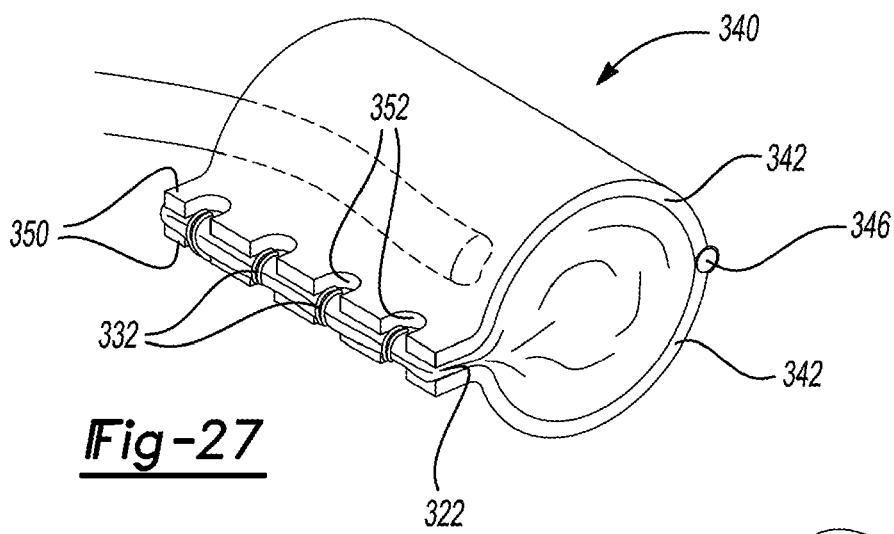

FIG. 27 shows the clamshell templating device of FIG. 26 where the clamshell portions are in a closed position for creating the cylindrical tissue graft with a connector, such as a plurality of sutures.

Figure 28:
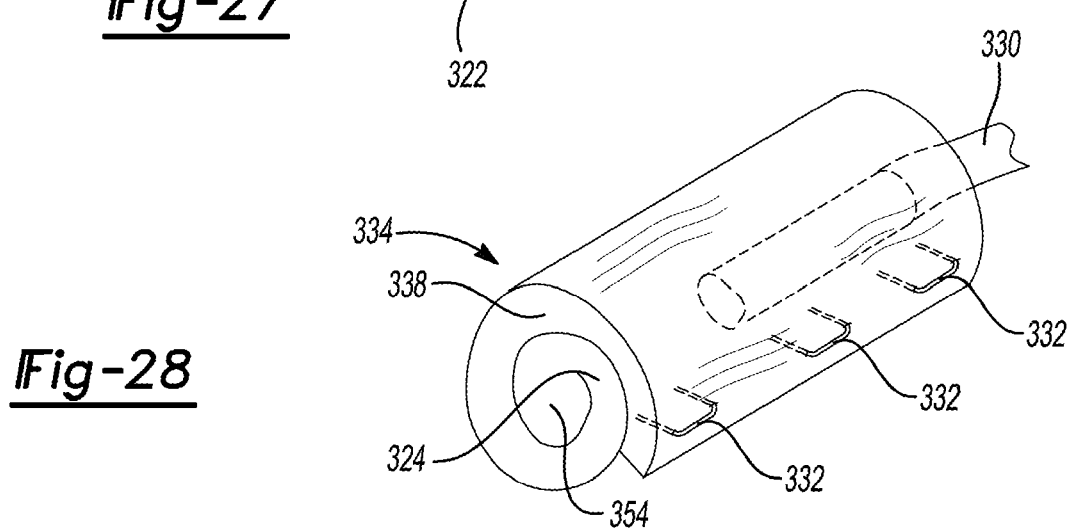

FIG. 28 shows a cylindrical nerve graft interface assembly having a cylindrical tissue graft created by a box plane cutter like in FIG. 24, where the harvested tissue graft is secured by a plurality of connectors (e.g., sutures) with a nerve end disposed therein.

Figure 29:
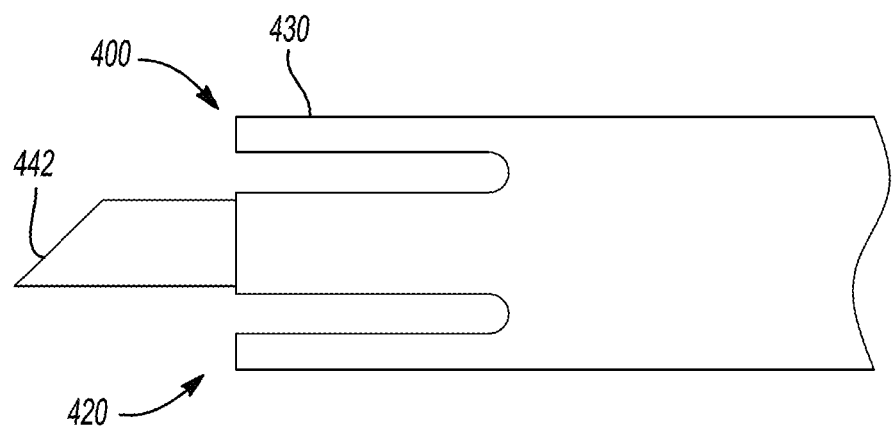

FIG. 29 is a detailed side view of a portion of a cutter mechanism for another alternative variation of a device or tool for creating a peripheral nerve graft interface or assembly in a subject in accordance with certain aspects of the present disclosure. The cutter mechanism shown includes an outer cutting sleeve that has a bendable sharpened arm surrounding a cutting tube in the tool for cutting a free tissue graft from a source of tissue in the subject.

Figure 30:
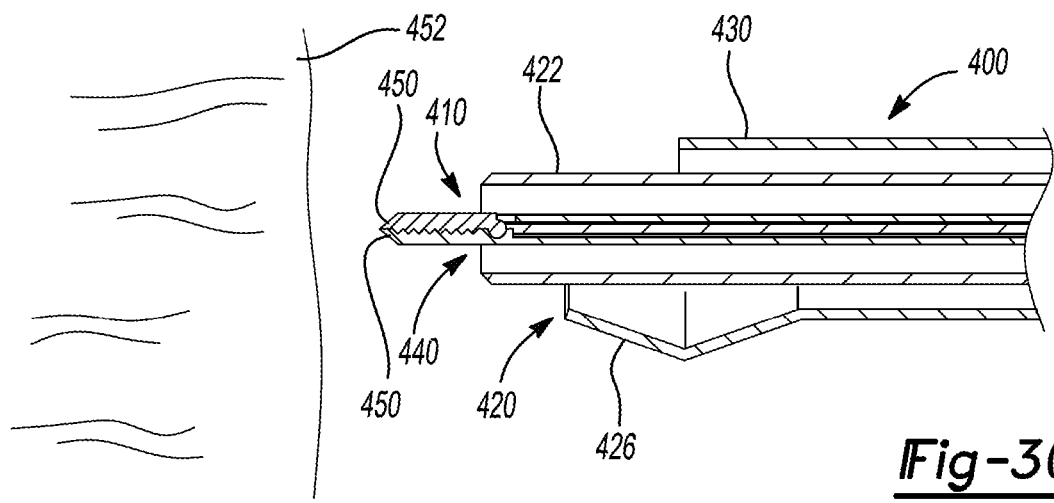

FIG. 30 shows a sectional view of the device or tool for creating a peripheral nerve graft interface or assembly including the cutter mechanism in FIG. 29, where portions a grasper mechanism including a plurality of grasper component members are also shown. The cutter mechanism includes the cutting tube, as well as the bendable sharpened arm surrounding the cutting tube that linearly translates from a first retracted position to a second extended position. In the second extended position the bendable sharpened arm is fully rotatable. The bendable sharpened arm has a sharp edge for cutting and removing the tissue graft. The tool is being directed towards a source of tissue in a subject prior to extraction of a free tissue graft.

Figure 31:
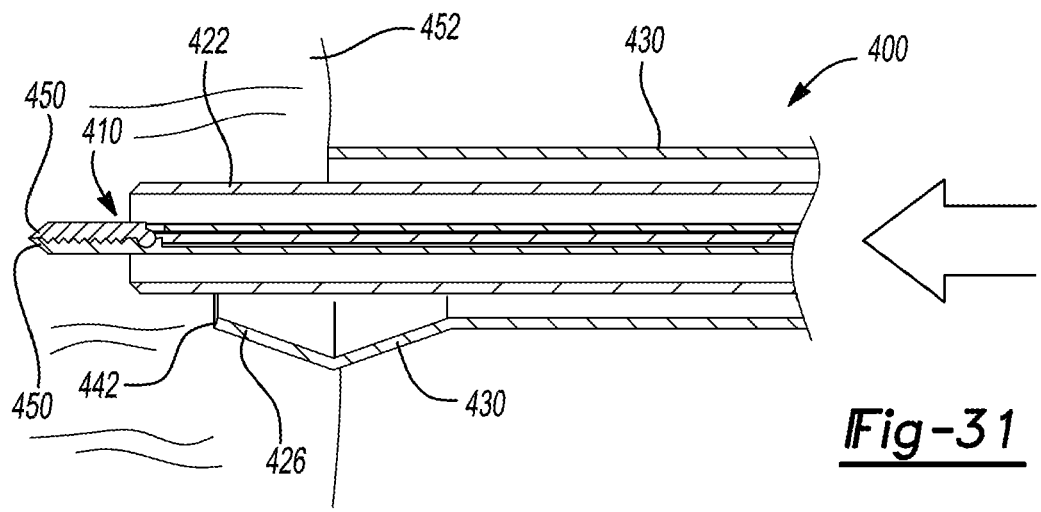

FIG. 31 shows the device or tool of FIGS. 29-30, where a terminal end of the tool, including the cutting tube, the bendable sharpened arm, and the plurality of grasper component members, have been introduced into tissue of the subject from which a free tissue graft will be removed (so that the inserted cutting tube has an open central region that contains tissue captured via the insertion process). The bendable sharpened arm is in the first retracted position.

Figure 32:
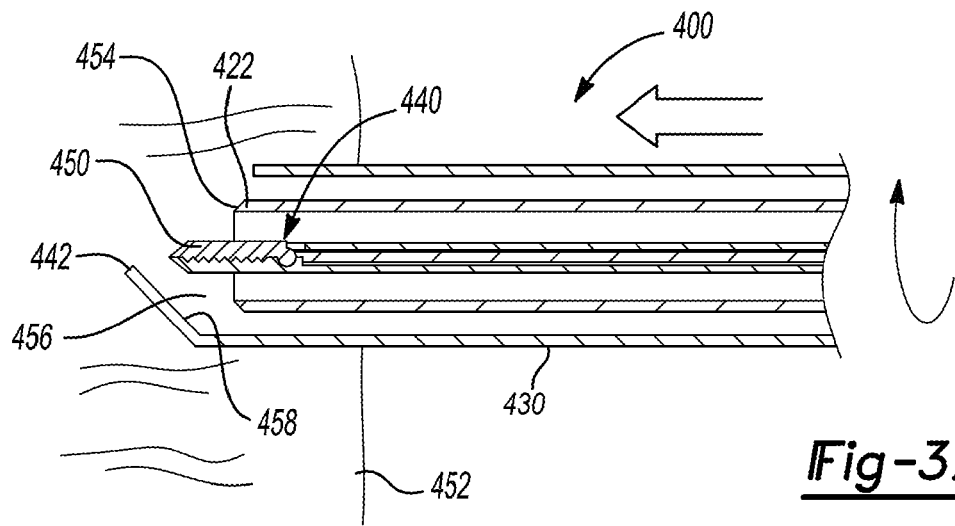

FIG. 32 shows the tool of FIGS. 29-31, where the bendable sharpened arm is linearly translated to the second extended position and extended beyond the plurality of grasper components and the cutting tube into the source of tissue in the subject.

Figure 33:
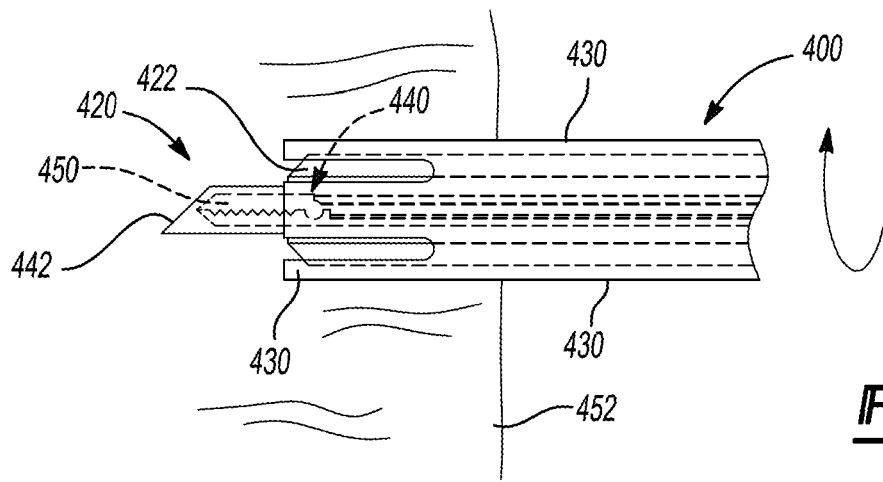

FIG. 33 is a side view of portions of the cutter mechanism and the grasping mechanism of the tool shown in FIGS. 29-32, including the bendable sharpened arm (with a sharp edge) as part of an outer tubular cutting sleeve disposed over the cutting tube for cutting and removing the tissue graft. The bendable sharpened arm with the sharp edge on the outer tubular cutting sleeve is rotated to cut and collect a hollow cylindrical free tissue graft from the source of tissue within the cutting tube.

Figure 34:
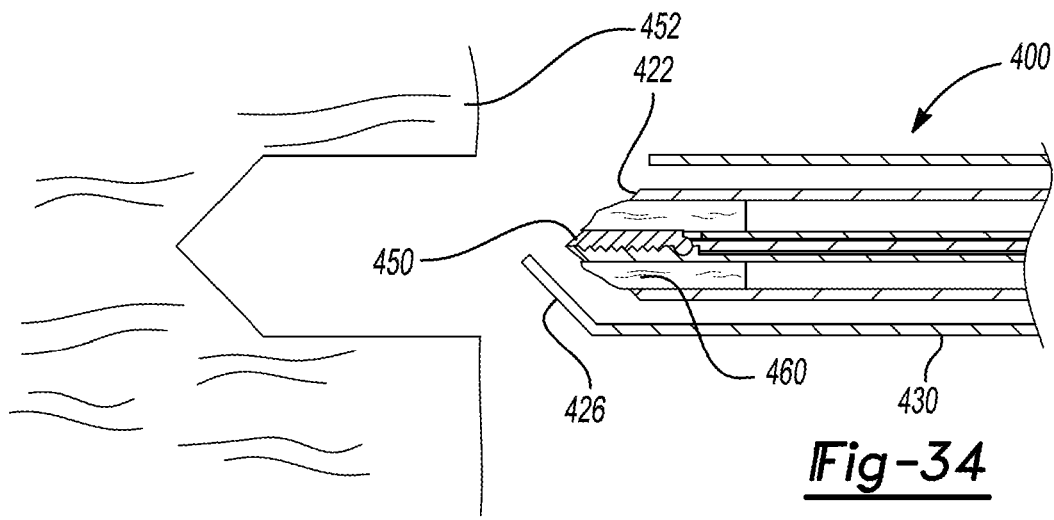

FIG. 34 shows a sectional view of the tool of FIGS. 29-33 being removed from the source of tissue in the subject, where the cutting tube has the free tissue graft contained therein.

Figure 35:
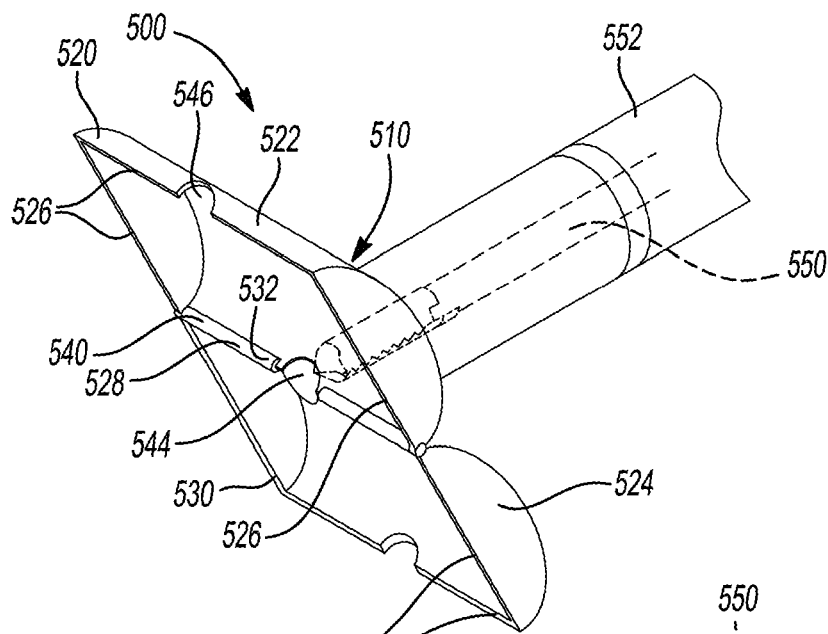

FIG. 35 is a detailed side view of yet another variation of a cutter mechanism of a device or tool for creating a peripheral nerve graft interface or assembly in a subject in accordance with certain aspects of the present disclosure, where the cutter mechanism comprises a cutter component in the form of a clamping cutting tube having two hinged portions on a first side and each hinged portion having a cutting edge on a second side, where the two hinged portions are in an open position. The clamping cutting tube also defines a first aperture and a second aperture opposite to the first aperture. The first aperture and the second aperture are configured to receive a grasper mechanism that is positioned orthogonally to the clamping cutting tube defined by the two hinged portions.

Figure 36:
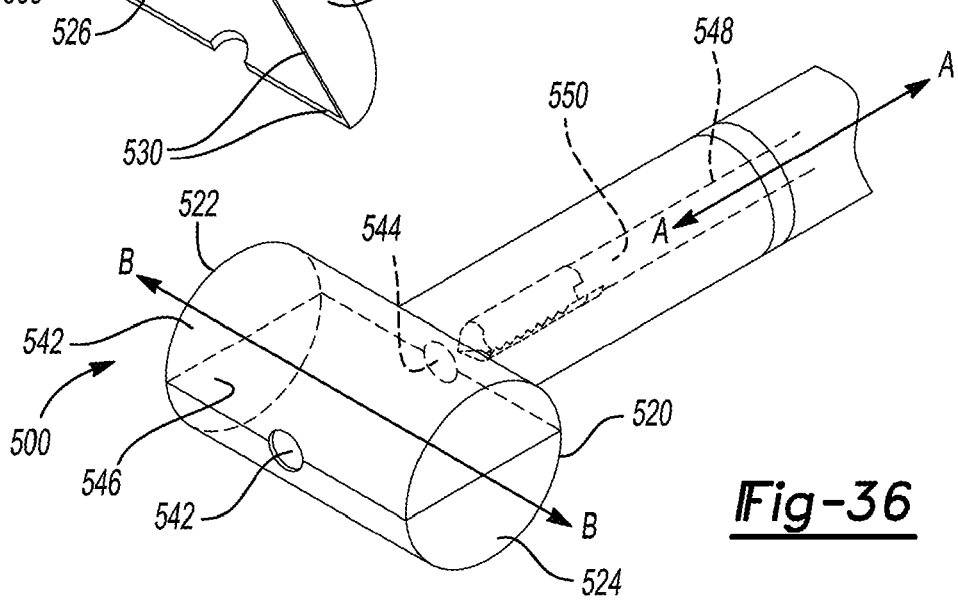

FIG. 36 is a detailed side view of the tool in FIG. 35, where the clamping cutting tube having two hinged portions is in a closed position. A second side of each of the two hinged portions includes a cutting edge, so that the complementary cutting edges on each hinged portion cooperate and engage with one another to cut tissue. Further, when the clamping cutting tube is in the closed position as shown, the first aperture and the second aperture are aligned to receive a grasper component of the grasper mechanism that translates through the clamping cutting tube defined by the two hinged portions.

Figure 37:
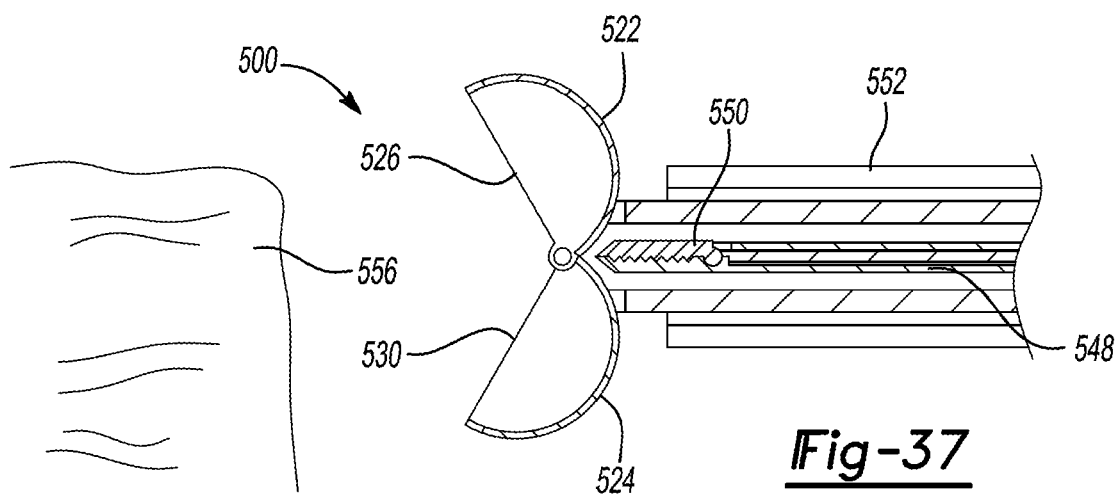

FIG. 37 is a side view of the tool in FIGS. 35-36 where the two hinged portions of the clamping cutting tube are in an open position and the tool is being directed towards a source of tissue in a subject prior to extraction of a free tissue graft.

Figure 38:
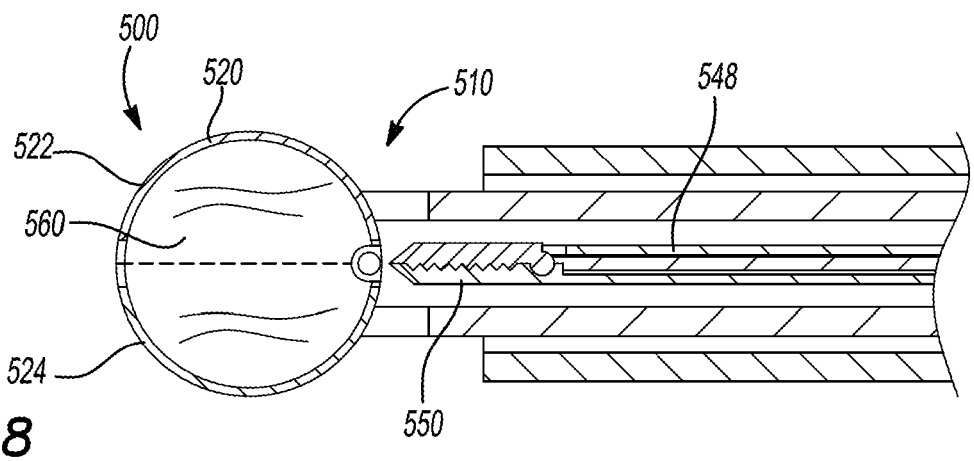

FIG. 38 is a side view of the tool in FIGS. 35-37, where a terminal end of the tool has been introduced into tissue of a subject from which a free tissue graft will be removed, where the two hinged portions of the clamping cutting tube are in a closed position that cuts and removes a free tissue graft contained in the clamping cutting tube.

Figure 39:
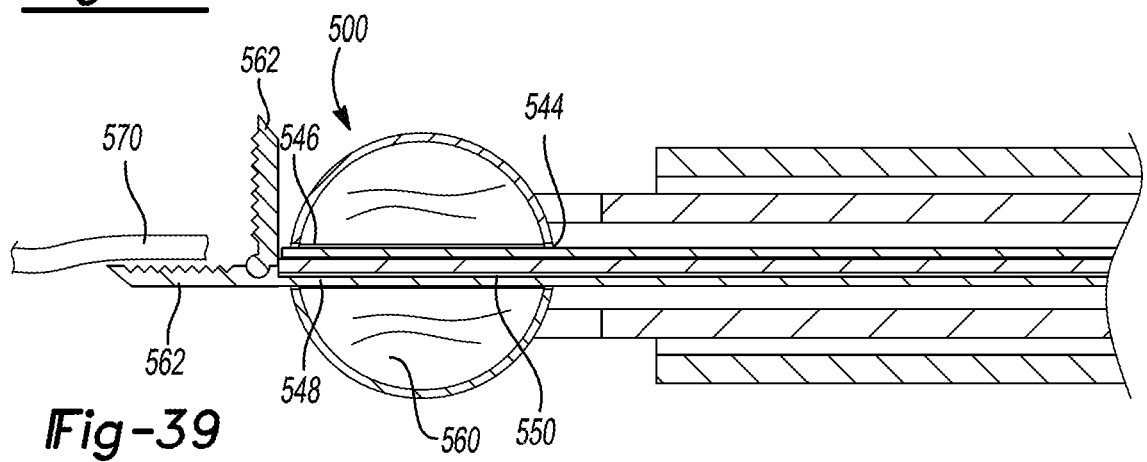

FIG. 39 shows the tool of FIGS. 35-38, where a tissue graft has been extracted from the subject within the clamping cutting tube of the tool and the tool is introduced into a surgical location of the subject having a peripheral nerve end, where the peripheral nerve end is grasped by a grasper mechanism comprising a grasper component in the form of a plurality of graspers on the terminal end of the tool passing through the first aperture and the second aperture defined within the clamping cutting tool.

Figure 40:
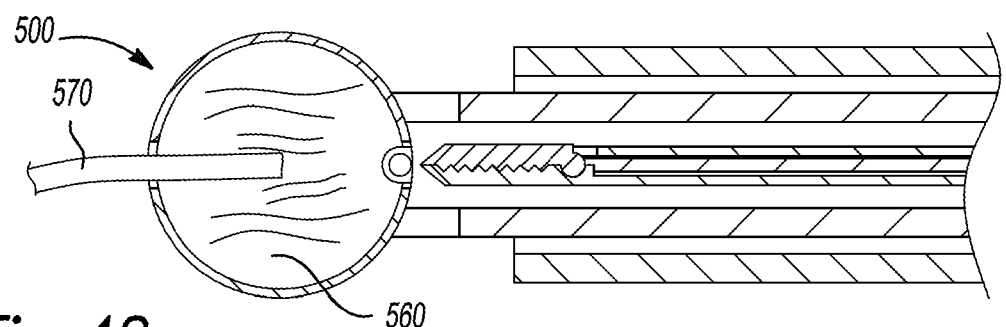

FIG. 40 shows the tool of FIGS. 35-39, where the grasper mechanism is retracted from the clamping cutting tube (in a closed position) and the peripheral nerve end is disposed within the center of the cylindrical free tissue graft.

Figure 41:
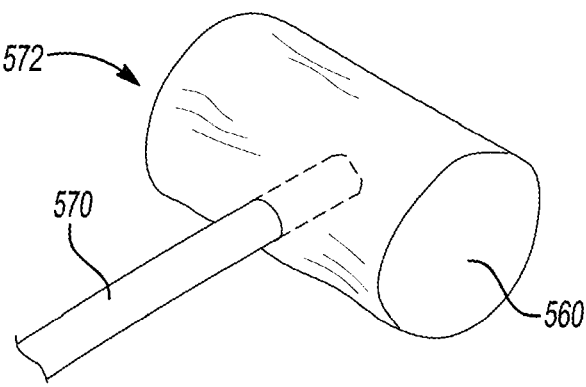

FIG. 41 shows a cylindrical nerve graft interface assembly having a cylindrical tissue graft formed by the tool of FIGS. 35-40 with the peripheral nerve end disposed therein.

Corresponding reference numerals indicate corresponding parts throughout the several views of the drawings.

It should be noted that the figures set forth herein are intended to exemplify the general characteristics of methods, devices, and materials, among those of the present disclosure, for the purpose of the description of certain embodiments. These figures may not precisely reflect the characteristics of any given embodiment, and are not necessarily intended to fully define or limit specific embodiments within the scope of this disclosure.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges.

The description and specific examples, while indicating features and embodiments, are intended for purposes of illustration only and are not intended to limit the scope of the disclosure. Moreover, recitation of multiple embodiments having stated features is not intended to exclude other embodiments having additional features, or other embodiments incorporating different combinations of the stated features. Specific examples are provided for illustrative purposes of how to make and use the described methods, systems, and compositions and, unless explicitly stated otherwise, are not intended to be a representation that given embodiments have, or have not, been made or tested. Features discussed in the context of one embodiment are intended to be applicable to other embodiments, unless otherwise indicated. Example embodiments will now be described more fully with reference to the accompanying drawings.

In various aspects, the present disclosure provides a medical device tool that is used in the treatment of neural conditions, such as treatment of neuromas or for nerve regeneration surgical procedures. More specifically, the medical device or tool can be used for both excising a tissue graft from a subject, and then implanting the tissue graft and connecting it with neural tissue, such as a peripheral nerve end, within the subject to facilitate formation of a neural graft assembly comprising the tissue graft and the nerve end. An exemplary neural tissue is a peripheral nerve associated with an amputated limb, by way of non-limiting example.

Figure 15:
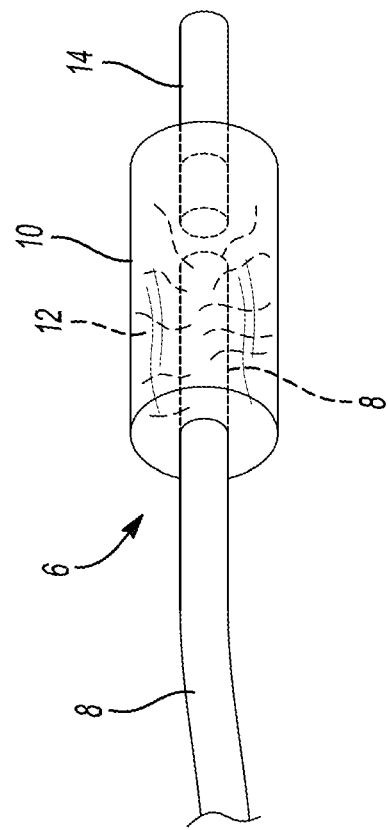
FIG. 15 shows a neural graft assembly including a portion of a peripheral nerve and a muscle graft assembly, or a regenerative neuromuscular construct (RNC), in a subject formed by using a medical device tool prepared in accordance with certain aspects of the present disclosure.

Thus, the medical device tool provided in accordance with the present disclosure is particularly suitable for forming a neural graft assembly or system in a subject. By way of background, FIG. 15 shows an implantable neural interface or neural graft assembly 6 (e.g., a regenerative neuromuscular construct (RNC)) for a peripheral nerve 8 in a subject. The subject may be an animal with a complex nerve system, such as a mammal, like a human, primate, or companion animal. A portion of the nerve 8, such as a nerve end, may be damaged or severed, for example, a fully or partially lesioned nerve end caused by injury, disease, or surgery. In certain aspects, the methods of the present disclosure discussed further below may include surgically dividing, sectioning, cutting, and/or transecting a portion of a nerve 8 into one or more individual branches or fascicles (not shown). One or more individual branches or fascicles of the nerve 8 are each placed within a free tissue graft 10. The free tissue graft 10 is preferably an autograft harvested or excised from a source of tissue in the subject by using the tools provided by the present disclosure and discussed below. Particularly suitable tissue sources include muscle tissue and dermis tissue. In certain preferred aspects, the free tissue graft 10 is muscle tissue.

The free tissue graft 10 is harvested or resected with the medical device or tool of the present disclosure to a standard, predetermined volume or size depending on the size of the branch or fascicle of divided nerve 8. When harvesting the free tissue graft 10, the tissue graft is devascularized and the native blood vessels no longer function. The predetermined volume of the free tissue graft 10 may be selected to be small enough that it is suitably revascularized by collateral blood flow so that the free tissue graft 10 thrives, while providing a sufficiently sized area or volume for the branches or fascicles of the nerve 8 to grow, as will be described in greater detail below. It should be noted that the predetermined volume of the free tissue graft 10 that facilitates reinnervation for successful formation of an implantable neural graft assembly 6 is significantly greater than a volume of a conventional biopsy samples.

Over a period of, for example, several months, the nerve 8 can thus reinnervate the free tissue graft 10 and sprout nerve fibers 12 in search of new neural targets. Once the free tissue graft 10 has been reinnervated, the action potentials from neurons traveling down the nerve then generate muscle level signal amplitudes instead of nerve level amplitudes. In this way, over time, the free tissue grafts 10 (e.g., free muscle grafts) act as an amplifier for the signals generated by the branches or fascicles of nerve 8 end, with the signal from a single nerve fascicle having a voltage amplitude of greater than or equal to about 250 μV pp and, in some instances, greater than or equal to about 500 μV pp and up to, for example, about 1,000 μV pp or more, as is described in co-pending U.S. patent application Ser. No. 14/940,703 filed on Nov. 13, 2015 that claims priority to U.S. Provisional Patent Application No. 62/079,206 filed on Nov. 13, 2014, entitled "Method For Amplifying Signals From Individual Nerve Fascicles" to Chestek et al., incorporated herein by reference in their respective entireties.

While the implantable neural graft assembly 6 can be used with any lesioned, sectioned, or damaged portion of a nerve (e.g., nerve ending) within a subject, it is particularly suitable for use with peripheral nerves. The implantable neural graft assembly 6 may thus be used for peripheral nerves suffering damage or injury, such as those involved with amputations. However, the methods and devices described herein may also be used with a variety of different nerves or alternatively with blood vessels or other biological structures. Thus, in certain aspects, while the methods of the present disclosure are particularly useful with peripheral nerves, the discussion of peripheral nerves and peripheral nerve interface devices is merely exemplary and non-limiting.

As shown in FIG. 15, the free tissue graft 10 can further include an optional electrical conductor 14, such as an electrode or wire, in electrical communication with the free tissue graft 10. The electrical conductor 14, in turn, is in electrical communication with an external wire (not shown) that is in electrical communication with an external prosthetic device (not shown), which may further include a processing module and an amplifier. In such a variation, the signal from the nerve 8 is received by the electrical conductor 14 and communicated over the wire to the processing module of the implant device. In other variations, the electrical conductor 14 can be used to introduce signals to or electrically communicate with the nerve 8. The electrical conductor 14 may have a maximum thickness of less than or equal to about 5 mm.

The nerve 8 thus regenerates within the free tissue graft 10 reinnervating the free tissue graft 10. Such reinnervation may include growing sprout nerve fibers 12. In this manner, the nerve 8 is thus capable of producing an amplified electrical signal of greater than or equal to about 250 microvolts without any external electrical input. Such a voluntary, spontaneous electrical signal (e.g., generated naturally from motor nerves) can be distinguished from stimulated nerve signals generated by introducing an external electrical input to the nerve for activation (e.g., stimulation by combined compound action potential (CMAPs) resulting from external nerve activation). The implantable neural graft assembly 6 may thus provide the ability to receive, process, record, and/or communicate nerve signals received from the free tissue grafts 10.

In certain aspects, such a neural graft assembly 6 may be a neural interface assembly referred to a regenerative peripheral nerve interface (RPNI), which generally includes the nerve 8, the free tissue graft 10 (e.g., muscle tissue graft), the electrical conductor 14, and may optionally include other associated external wiring and componentry, including a processing module. Alternatively, in certain other variations, the electrical conductor 14 can be omitted altogether, so that the neural graft assembly 6 only contains the free tissue graft 10 and fascicle of nerve 8. Such a passive embodiment of a neural graft assembly is particularly suitable for treating neuromas.

The present disclosure thus provides a device or tool for creating an implantable neural graft assembly in a subject. In certain variations, such a device or tool may comprise a cutter mechanism and a grasper mechanism. The cutter mechanism is configured to cut the tissue. The cutter mechanism also can serve to remove a tissue graft from a source of tissue in the subject. The tissue graft preferably has a hollow central region or in alternative variations, is formed into a cylindrical tissue graft after being cut. The grasper mechanism is capable of retaining a nerve end of the subject in a first position and releasing the nerve end in a second position. The grasper mechanism may be associated with one or more first actuation mechanisms or components that serve to move at least one grasper component of the grasper mechanism from the first position to the second position and also to optionally control rotation of the grasper component, as necessary. The tool also includes a second actuation mechanism or component that can move and control the cutter mechanism. The tool also includes a third actuation mechanism or component that when activated disposes the tissue graft over the nerve end. The third actuation mechanism or component of the tool may thus be configured to move the tissue graft relative to the grasper mechanism. Such first, second, and third actuation components may be operated manually or via automation. In this manner, the device creates an implantable neural graft assembly comprising the nerve end disposed within the free tissue graft.

The present disclosure thus provides a device or tool for creating an implantable neural graft assembly in a subject that provides the following functions. First, the tool provides the capability to remove large bores of tissue samples or grafts from a donor site in a subject by performing two cuts substantially perpendicular to each other. This type of cutting mechanism differs from biopsy-small bore tissue removal that is typically only a single cut. Further, the tool provides the ability to create a free tissue graft having a hollow center core, by punching core samples (either concentrically or along flap) to create a region cavity to house an end of a nerve. The tool also provides a grasper or retractor mechanism that can grasp a nerve or other structure to place it inside the hollow core cavity of the graft. Finally, the tool provides an actuation mechanism that ejects the completed neural graft assembly as an implanted structure.

In certain variations, the cutter mechanism may include a cutter component that can be releasably received within the device or tool. Thus, the cutter component may be interchangeable, disposable, and/or replaceable. In certain aspects, the cutter component is interchangeable and selected from for a variety of distinctly sized cutter components, so that an appropriately sized cutter is used in the cutter mechanism of the tool based on the dimension of the free tissue graft required and the implantable neural graft assembly formed.

In other variations, the cutter components are interchangeable and selected from a variety of different types of cutter components. Generally, a cutter mechanism used in certain variations of the tool of the present disclosure can include an outer tube (or other non-round shapes of hollow structures) and another cooperating cutting edge to sever the base of the tissue being extracted from the source. In certain variations, the cutter component is a cutting tube having an internal bore and a terminal end that cuts the tissue graft from the source of tissue in the subject. Such a cutting tube may include a concentric tube structure, where a grasper mechanism may include a grasper component seated within the internal bore of the concentric cutting tubes. An additional cutter component may also be external to the cutting tube, for example, a loop of wire around the cutting tube that creates contact to sever the tissue base. In other aspects, the cutter component may be an electrosurgical tool or electrosurgical knife, such as a BOVIE™ electrosurgical cutting device. In certain other variations, the cutter tool may be a knife or blade. For example, two or more blades can be used as the cutter component to cut into a surface of muscle to harvest the tissue sample, such as an eyelid type cutting device. Various embodiments of different cutter mechanism components, including different cutting tubes and other cutter components are described in more detail herein.

The grasper mechanism may be moved via mechanical linkages associated with the first actuation mechanism or component. In certain aspects, the grasper mechanism of the tool may have a plurality of grasper component members that cooperate to retain the nerve in the first position. In other aspects, the grasper component may be a suction tube or vacuum grasper that in a first position has the suction activated (is drawing negative pressure or a vacuum) and in a second position does not have any suction or vacuum being drawn. In other aspects, a compliant grasper component can be used that is capable of flexing when actuated, instead of employing mechanical linkages. In other yet aspects, a grasper component has a loop or eye through which the nerve may be threaded. In certain variations, the grasper component is releasably received within the grasper mechanism of the device. Thus, the grasper component may be interchangeable, disposable, and/or replaceable. Where the grasper component is interchangeable, it may be selected from for a variety of distinctly sized grasper components, depending on the size of the nerve or fascicle on which the implantable neural graft assembly is formed.

Figure 1:
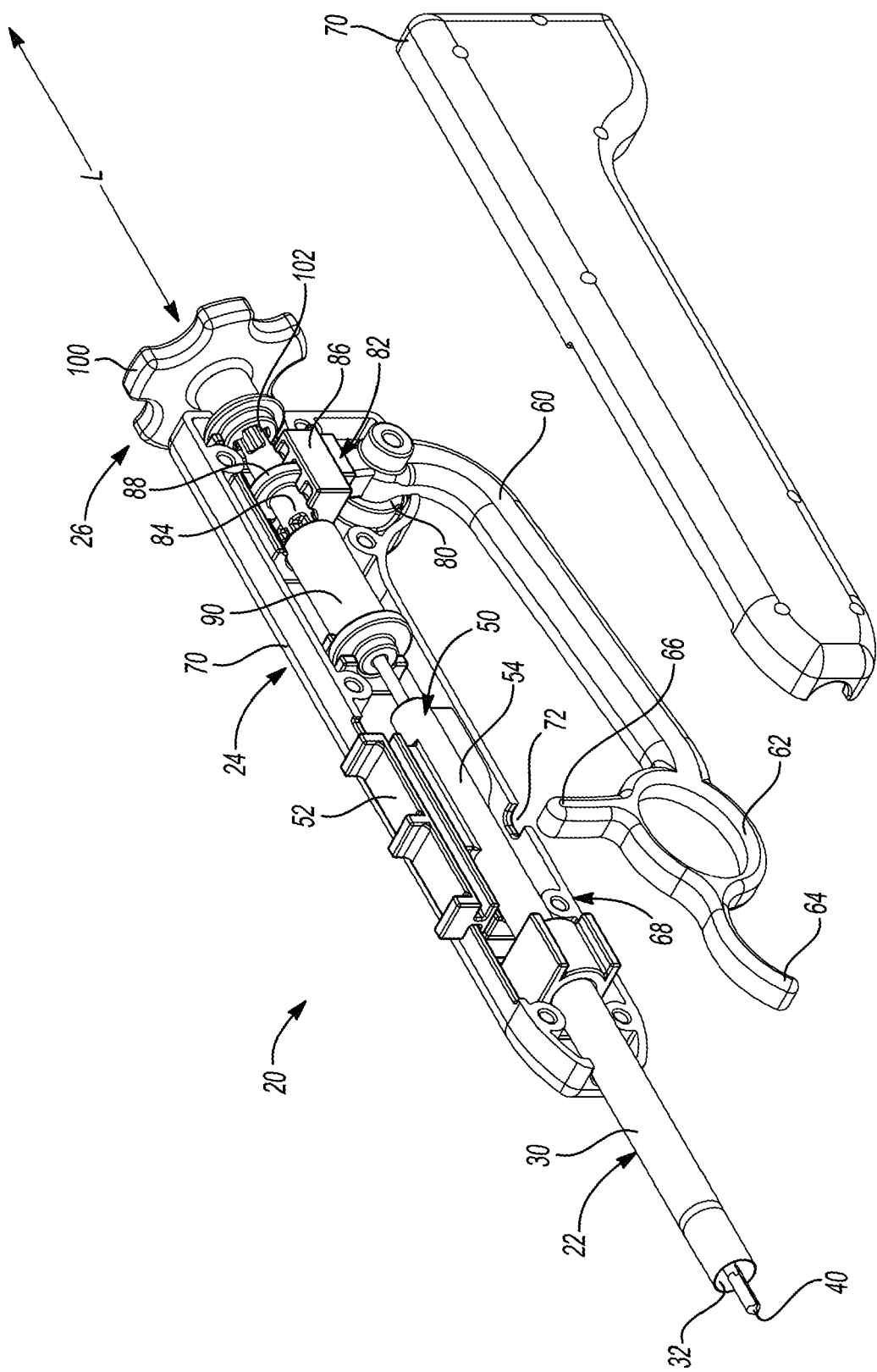
FIG. 1 is a perspective view of a medical device tool for creating a peripheral nerve graft interface or assembly in a subject in accordance with certain aspects of the present disclosure having a cutter mechanism, a grasper mechanism, and an actuation mechanism for ejecting the peripheral nerve graft interface or assembly.
Figure 2:
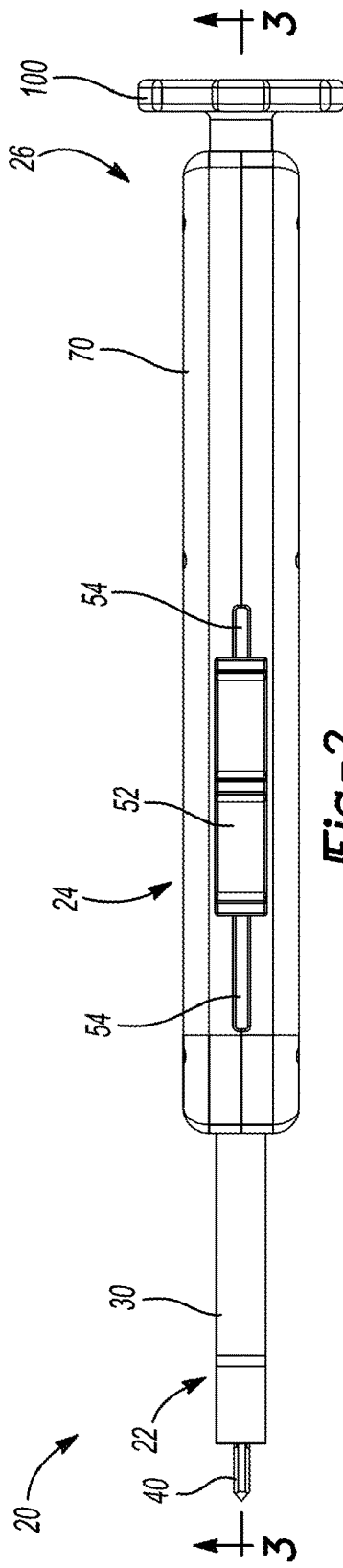
FIG. 2 is a plan view of the tool of FIG. 1.
Figure 3:
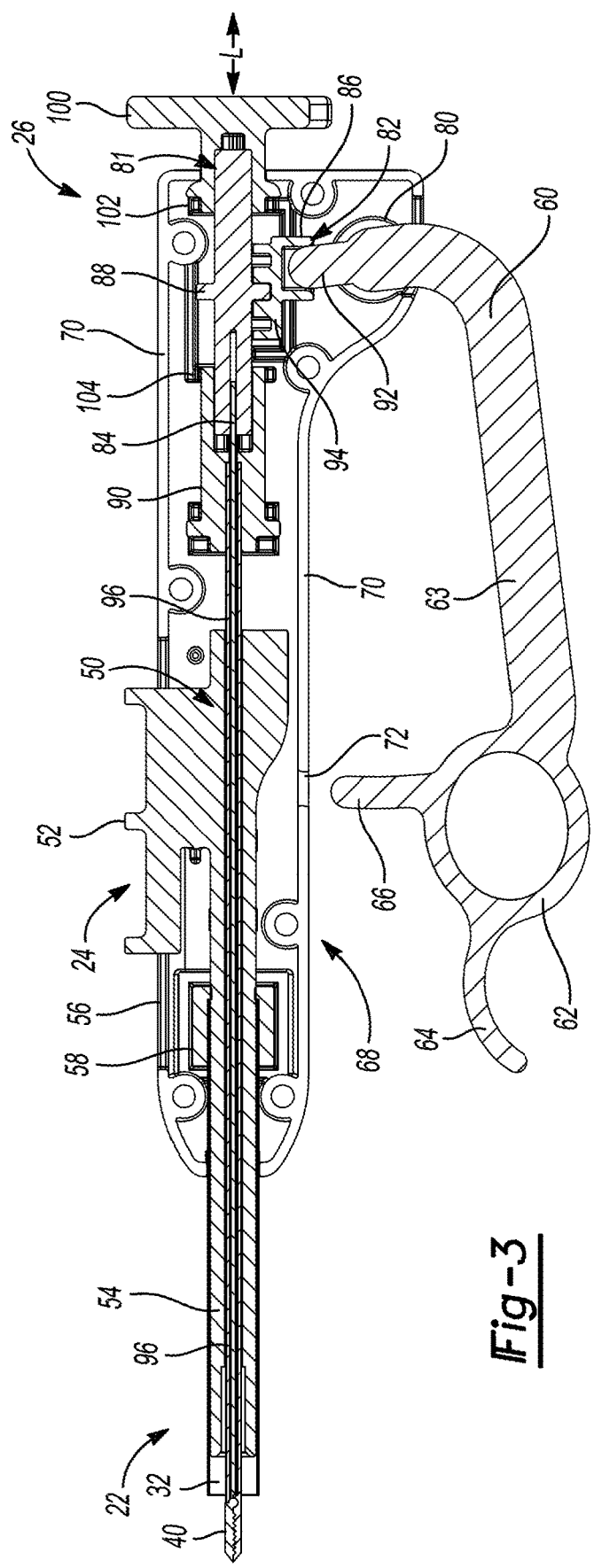
FIG. 3 is a sectional view taken along line 3-3 of FIG. 2.

The present disclosure thus provides a surgical device or tool 20 as shown in FIGS. 1-3 for creating a peripheral nerve interface assembly in a subject in accordance with certain aspects of the present teachings. In one exemplary embodiment, the tool 20 defines a distal end 22, a central body region 24, and a proximal end 26, and includes a housing 70. Distal end 22 includes a cutting mechanism including a cutting tube 30 and a grasper mechanism including a plurality of grasper component members 40. Cutting tube 30 is shown as an open cylindrical shape having a void or internal bore 32. The cutting tube 30 has a sharp terminal edge 140 that cuts soft tissue as it is introduced into a source of soft tissue in the subject. The cutting tube 30 may be formed of a metal, such as surgical grade stainless steel. The cutting tube 30 could have a coating that improves hardness/wear properties of the tip. For example, a titanium nitride coating may be used. Alternatively, the cutting tube 30 can be formed of a biocompatible plastic connected to a metal tip as the cutting region (e.g., sharp terminal edge 140). It should be noted that in alternative variations, cutting tube 30 may have other cross-sectional shapes, and is not limited to a cylinder or tube. Other alternative variations of cutting tube and cutting component designs will be discussed further below.

The central body region 24 includes an ejector assembly 50 that serves as an actuation mechanism configured to dispose the tissue graft over the nerve end. The ejector assembly 50 has a tissue ejection slide component 52 seated in a longitudinal slot 56 of housing 70. The ejector assembly 50 also includes an ejector, such as a plunger 54, that is capable of linearly translating (e.g., extending or retracting) along a central longitudinal axis (L) within a portion of the internal bore 32 opening of the cutting tube 30. By sliding or translating the tissue ejection slide component 52 in the longitudinal slot 56, the plunger 54 moves in the same direction as the tissue ejection slide component 52. The plunger 54 can move laterally (e.g., telescope in and out) with respect to the central body region 24 of tool 20. One or more predetermined internal stops or dividers 58 may form part of the ejector assembly 50 inside the central body region 24, which serves to stop motion of the tissue ejection slide component 52 at predetermined points and thus creates intermediate and terminal distal endpoints for movement of the plunger 54.

In the embodiment shown in FIGS. 1-3, cutting tube 30 is rigidly fixed with respect to the central body region 24. However, in other alternative variations, cutting tube 30 and/or plunger 54 can move laterally (e.g., telescope in and out) with respect to the central body region 24 of tool 20. Thus, instead of moving the plunger 54 outwards in a distal direction (towards a distal end 22 of tool 20), the cutting tube 30 could be moved or retracted inwards in a proximal direction (towards a proximal end 26 of tool 20), or some combination of movement of the plunger 54 and cutting tube 30 may employed to achieve ejection of tissue from the cutting tube 30.

An actuation component for the grasper mechanism is in the form of a handle 60 is attached to the housing 70 at proximal end 26 of the tool 20. Handle 60 has a finger loop 62 with an optional finger seat projection 64 for so that one or more of the user's (e.g., surgeon's) fingers grasp and securely hold the tool 20 and handle 60. The finger loop 62 also includes a medial projection 66, which can seat against a lower side 68 of housing 70 of the tool 20. As shown, a receiving aperture 72 is defined in the lower side 68 of housing 70. The finger loop of handle 60 is attached to an arm 63 that ends in a terminal portion defining a cam 92 (best seen in FIG. 3).

The handle 60 controls movement (opening and closing) of one or more of the plurality of grasper component members 40 of the grasper mechanism at the terminal distal end 22 of the tool 20. Thus, handle 60 translates from an open position to a closed position, which in turn controls the positioning of the plurality of grasper component members 40 from a first closed position to a second open position described further below. In the open position, the finger loop 62 is pulled away from the lower side 68 of housing 70 by rotating movement, so that arm 63 forms an angle to the lower side 68 of housing 70. The handle 60 in the closed position has medial projection 66 that seats near or against housing 70. In certain variations, the handle 60 and medial projection is seated against and in contact with housing 70 or optionally at least partially seated within receiving aperture 72. Handle 60 can traverse and remain at intermediate positions from the fully open position to fully closed position, so that the opening between the plurality of grasper component members 40 can be readily controlled by controlling the distance at which the handle 60 is drawn away from the lower side 68 of housing 70.

The handle 60 is connected to a pin joint 80 within the housing 70 at the proximal end 26. The pin joint 80 is connected to a grasper assembly 81 of the grasper mechanism that includes a cam and follower joint assembly 82. The grasper assembly 81 includes a grasper shaft 84 seated in a grasper carriage 86 via at least one inner shaft mount 88. The grasper shaft 84 is disposed within an outer shaft mount 90. When the grasper handle 60 is rotated outward (e.g., translated in a lateral direction away from the housing 70 of tool 20) about the pin joint 80, the rotational motion is converted to linear motion in the grasper assembly 81 via a cam and follower operation of the cam and follower joint assembly 82. As discussed above, the cam 92 forms part of the design of a terminal end of the handle 60. Cam 92 is received within the grasper carriage 86, which thus acts as follower. The grasper carriage 86 then moves linearly (e.g., along the longitudinal central axis (L) to the left in FIG. 1)

sliding along tracks 94 built inside the housing 70. The grasper inner shaft mount 88, which is constrained in all linear degrees of freedom within the grasper carriage 86 and housing 70 of tool 20, moves along with the grasper carriage 86 thus moving grasper shaft 84.

Grasper assembly 81 also has an elongated tube or outer cylinder 96 to which grasper shaft 84 is connected. A portion of outer cylinder 96 is centrally disposed within the internal bore 32 of the cutting tube 30. Further, a portion of the outer cylinder 96 is centrally disposed within a central bore of plunger 54. The plunger 54 is capable of sliding past the outer cylinder 96. The outer cylinder 96 rotates about longitudinal axis L. The movement of the grasper carriage 86 moves grasper shaft 84 relative to the outer cylinder 96, causing a linkage between respective grasper components 40 at the distal end 22 to open or splay (described further below in the context of FIGS. 4 and 5).

Proximal end 26 of tool 20 further includes an actuation component that rotates the grasper components 40. The actuation component is in the form of a rotatable wheel 100, but may also be a lever, a rod, cross, or the like. Rotatable wheel 100 is connected to the grasper assembly 81, more particularly to grasper inner shaft mount 88, via a first splined portion 102 of grasper shaft inner shaft mount 88. The rotatable wheel 100 is linearly constrained by the housing 70 of the tool 20, but is free to rotate about the central longitudinal axis (L) of the tool 20. The first splined portion 102 allows the grasper inner shaft mount 88 and distal portion of the grasper shaft 84 to independently move linearly forward and away from the rotatable wheel 100, while transferring the rotational motion imparted as the rotatable wheel 100 rotates to the grasper inner shaft mount 88. Rotatable wheel 100 may thus be mechanically rotated, for example, by a user's thumb or other fingers, to greater than or equal to about 360°. In certain variations, the rotational direction may be clockwise, counterclockwise, or both clockwise and counterclockwise. While not shown, such a rotation process may be automated, as well. In this way, when rotatable wheel 100 is rotated, for example, by a user's thumb or other fingers, grasper components 40 are thus rotated at the distal end 22 of the tool 20. When at least one of the grasper components 40 is in the second open position, it may be fully rotated to at least 360° by turning the rotatable wheel 100, as discussed further below.

A similar second sliding spline portion 104 is used between the grasper inner shaft mount 88 and the grasper outer shaft mount 90 in the grasper assembly 81. The grasper outer cylinder 96 is rigidly fixed to the grasper outer shaft mount 90. Inner shaft 84 connects to inner shaft mount 88. Grasper outer cylinder 96 connects to grasper outer shaft mount 90. The grasper outer shaft mount 90 is constrained in all degrees of freedom by housing 70 except for rotation about the central longitudinal axis (L) of the tool. The rotational motion from the grasper inner shaft mount 88 is also transferred to the grasper outer shaft mount 90, causing the entire grasper assembly to rotate together when the rotatable wheel 100 is rotated.

Figure 4:
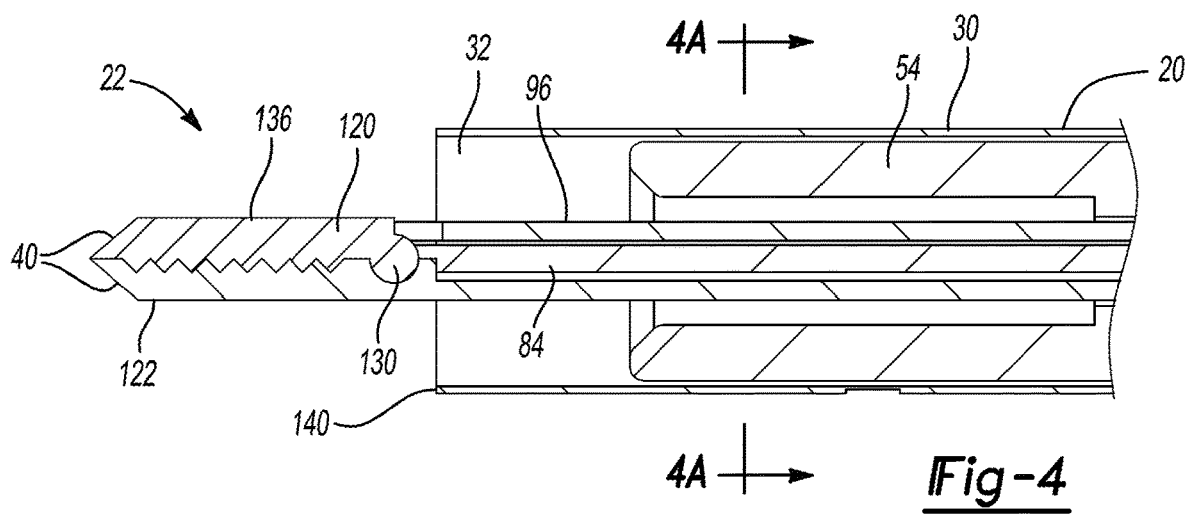
FIG. 4 is a detailed view of a distal end of a tool for creating a peripheral nerve interface in accordance with certain aspects of the present disclosure where the grasper mechanism includes a plurality of grasper component members in a closed position.
Figure 4A:
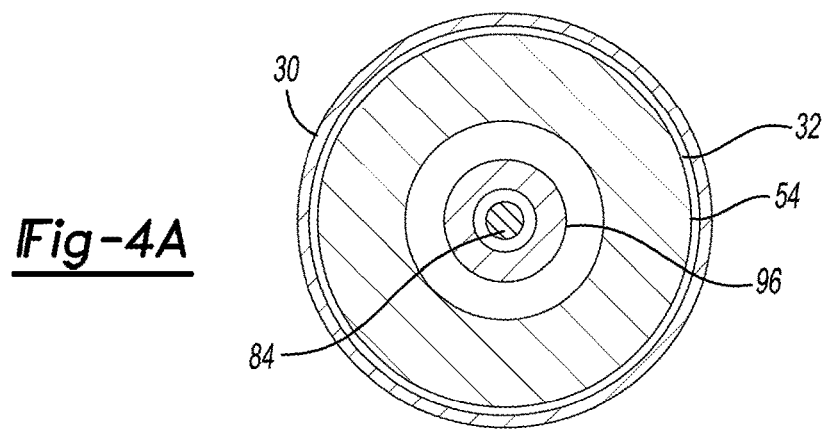
FIG. 4A is a sectional view taken along line A-A of FIG. 4.
Figure 5:
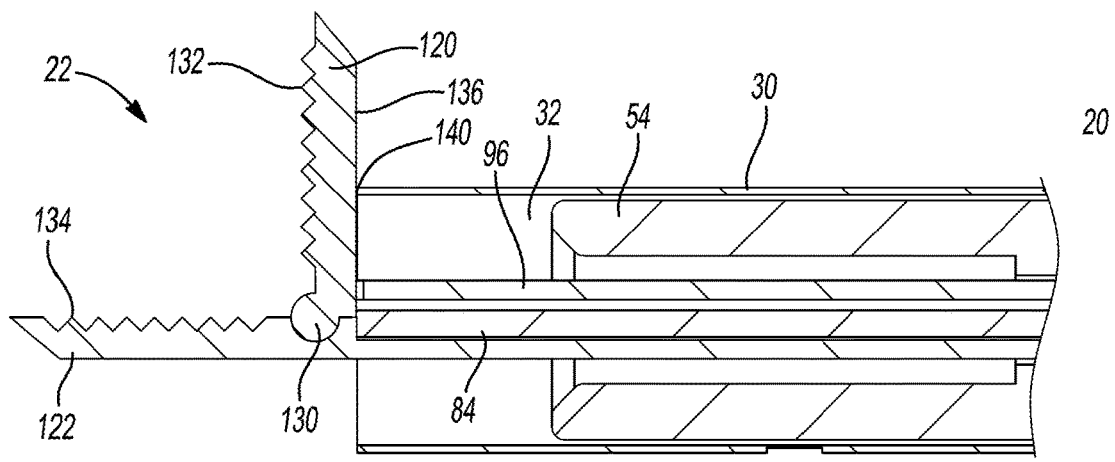
FIG. 5 is a detailed view of a distal end of a tool for creating a peripheral nerve interface in accordance with certain aspects of the present disclosure where the grasper mechanism includes a plurality of grasper component members, where one of the grasper components is in an open position capable of cutting tissue.

FIGS. 4, 4A, and 5 show a detailed view of the distal end 22 of tool 20 including portions of the grasper and cutter mechanisms. The grasper inner shaft 84 is a solid rod that fits inside of grasper outer cylinder 96. Grasper inner shaft 84 mounts into grasper inner shaft mount 88, and connects to linkage 130. In FIG. 4, a pair of grasper components 40 is shown, including a first grasper component 120 and a second grasper component 122. Notably, more than two grasper components 40 are contemplated in alternative variations. Other alternative types of grasper components may likewise be used in place of this design. The first grasper component 120 and the second grasper component 122 may be formed of metals, such as stainless steel, or biomedically acceptable plastics that are well known in the art. In certain variations, the first grasper component 120 may be formed of a combination of plastics and metals. In FIG. 4, the first grasper component 120 and the second grasper component 122 are in a first closed position where handle 60 in FIGS. 1 and 3 is in a closed position. First grasper component 120 and second grasper component 122 are connected to one another at a linkage 130 that permits first grasper component 120 to open at an angle with respect to the second grasper component 122. First grasper component 120, second grasper component 122, inner cylinder 96, and inner shaft 84 are connected together via the linkage 130. Inner cylinder 96 is connected to grasper shaft 84 and seated within an internal bore 32 of cutting tube 30 and within central bore of plunger 54 (as shown in FIG. 4A).

When movement of handle 60 causes grasper shaft 84 to push linkage 130, first grasper component 120 opens or splays, as shown in the open position in FIG. 5. As shown, an angle between the first grasper component 120 and the second grasper component 122 is about 90° in the fully open position. However, as previously discussed above, the angle may gradually open from 0° to 90° as the distance that the handle 60 is drawn away from the housing 70 is gradually increased and may be opened to angles between 0° to 90°. This provides the ability to grasp nerves or fascicles of different diameters and to ensure that the force applied to the nerve end is not too great to cause sustained physical damage. The handle 60 thus provides feedback control to the user, so that amounts of compression between the first grasper component 120 and the second grasper component 122 in the first closed position can be adjusted as necessary. When the first grasper component 120 is in the open position in FIG. 5, it serves to retain a free tissue graft within the open space of internal bore 32 of cutting tube 30 as the tool 20 is withdrawn from the source of tissue.

The first grasper component 120 has a first internal grasping face 132 and second grasper component 122 has a second internal grasping face 134. Nerves are slippery, thus in certain variations, each of the plurality of grasper component members 120, 122 has a grasping surface treated or patterned to enhance retention of the nerve end. As shown, each of the plurality of grasper component members 120, 122 is designed to include a patterned grasping surface that enhances friction forces and retention of the nerve end when in the first closed position during the surgical procedure. In certain variations, the first and second grasping faces 132, 134 may each be patterned, for example, with corrugations or with serrated surface patterns. In certain variations, the serrated surfaces may together define an interlocking saw tooth pattern when in the first closed position. Other treated grasping faces, including other patterns or types of grasping faces known in the art may also be used in certain alternative variations. In certain aspects, the grasping faces may include other materials like a layer of compliant foam that deforms around a nerve. Further, surface treatment (e.g., roughening or etching of the surface) may be used on the grasping surfaces. Other surface treatments include plating or coating of the grasping surfaces with non-slip or high friction coefficient coatings or materials.

First grasper component 120 has an outer cutting surface 136. In the open position, the outer cutting surface 136 contacts a terminal edge 140 of cutting tube 30. By turning the rotatable wheel 100, the first grasper component 120 rotates along the terminal edge 140 and severs or cuts any tissue collected within the open internal bore 32 of the cutting tube 30 from the surrounding tissue. Thus, where the rotatable wheel 100 rotates 360°, the outer cutting surface 136 rotates 360° around the entire terminal edge 140 of cutting tube 30. The outer cutting surface 136 may be formed of a distinct material (e.g., hardened materials or coatings, like titanium nitride) or may be sharpened to have predetermined angles that enhance cutting capability. In certain other variations, the outer cutting surface 136 can be formed of a metal, such as normal stainless steel with no sharpening, coating, or other treatment.

In certain aspects, a single point between outer cutting surface 136 and terminal edge 140 provides particularly effective cutting ability. Accordingly, in certain variations, the outer cutting surface 136 may be sharpened to exhibit a bevel or taper having an angle of greater than or equal to about 15° to less than or equal to about 30°, by way of non-limiting example. In one variation, the outer cutting surface 136 may be sharpened to an angle of about 25°. In certain other aspects, outer cutting surface 136 may be flat along the top, so long as terminal edge 140 is sharpened. Thus, the terminal edge 140 of cutting tube 30 may likewise be formed of a distinct material from the remainder of the cutting tube 30 or sharpened to promote cutting of tissue as the distal end 22 of tool 20 is introduced into the source of tissue and/or to enhance cutting in cooperation with the outer cutting surface 136 of first grasper component 120.

As noted above, the cutting tube 30 may be formed of various distinct materials, such as metals and/or plastics. The cutting tube 30 may be formed of metals, such as stainless steel, while the terminal end of cutting tube 30 may be formed of hardened steel or a titanium nitride material. In other variations, the cutting tube 30 may be formed of biocompatible plastic, while the terminal end of cutting tube 30 may be formed of metal, such as hardened steel or a titanium nitride material. In certain variations, the terminal edge 140 of the cutting tube 30 can be tapered or beveled to enhance cutting capability, again to similar angles as those described above for the outer cutting surface 136 of first grasper component 120. Typically, a terminal edge 140 (or outer cutting surface 136) can be sharpened to an angle, while considering striking a balance between sharpness and durability (as the sharper the angle, the less durable the surface). For example, in certain non-limiting examples, the terminal edge 140 may have an angle of greater than or equal to about 15° to less than or equal to about 30°. In certain aspects, both the outer cutting surface 136 and the terminal edge 140 may have such sharp edges (e.g., may have a bevel or taper) and cutting angles that cooperate to facilitate scissoring action while cutting the tissue. Any of these cutting surfaces may also be serrated.

FIGS. 16 and 17 show an alternative variation of a distal end 22A of a plurality of grasper component members 40A, which includes a first grasper component 120A and the second grasper component 122. Where the components are the same as those described in the context of FIGS. 4 and 5, the same reference numbering will be used and for brevity these components will not be specifically addressed again unless otherwise discussed. FIG. 16 shows the grasper components 40A in a closed position, while FIG. 17 shows the grasper components 40A in an open position. In this variation, outer cutting surface 136A has a notch or recessed region 142 capable of seating against a terminal edge 140 of cutting tube 30. When the terminal edge 140 is received within and seats against the recessed region 142 of the outer cutting surface 136A, cutting may be improved and wear minimized on the terminal edge 140 of the cutting tube 30.

In certain aspects, the present disclosure contemplates a method of forming an implantable neural graft assembly in a subject. The method may include excising or cutting a tissue graft having a hollow core from a source of tissue with a tool and retaining the tissue graft in the tool. Then, a biological structure can be introduced (e.g., via pulling or ejecting the tissue graft over the biological structure) into a portion of the hollow core of the tissue graft by use of the tool. In this manner, the biological structure is disposed in the hollow core of the tissue graft. Then, the tissue graft and biological structure are ejected from the tool as an implantable assembly of the biological structure and the tissue graft. In certain variations, the tissue graft is muscle or dermal tissue, and the biological structure is a portion of a nerve. In other aspects, the biological structure may be a blood vessel or any other structure or tissue that requires connection to another tissue. For example, any biological material or structure of a predefined shape can be connected to another biological material, including skin, fat, and the like. In other aspects, the tissue graft may be muscle and the biological structure is a portion of a tendon. Furthermore, in certain aspects, a biological structure to be pulled may be a nerve, tendon, or muscle, which is pulled into another biological material. Such a biological material may be a container filled with stem cells.

In certain aspects, the present disclosure provides methods of forming an implantable neural graft assembly in a subject with a tool. The tool may have a cutter mechanism and a grasper mechanism. Such a method may comprise introducing a device that harvests or excises a free tissue graft from a source of tissue in the subject, such as from muscle tissue. Such harvesting of a free tissue graft may be achieved by use of the cutter mechanism on the tool. Then, the device may be used to associate the free tissue graft to a nerve end in the subject, for example, by use of the grasper mechanism on the tool, so as to create the implantable neural graft assembly comprising the nerve end disposed within the free tissue graft.

In other aspects, the present disclosure contemplates methods of forming an implantable neural graft assembly in a subject. Such a method may comprise introducing a device comprising a cutting mechanism comprising a cutting tube and a grasper mechanism comprising a plurality of grasper component members into a source of tissue in the subject. Then, a free tissue graft may be excised or cut from the source of tissue, such as a soft tissue source, like muscle tissue. The free tissue graft is retained in the cutting tube as the device is removed from the source of tissue. Next, the method involves grasping a nerve end with the plurality of grasper component members of the device. In certain aspects, the nerve end can be physically secured to the free tissue graft. Then, the free tissue graft is ejected from the device to create the implantable neural graft assembly comprising the nerve end disposed within the free tissue graft.

In certain aspects, the plurality of grasper component members has at least one grasper component with a cutting edge and the cutting tube has a terminal end. The plurality of grasper component members extends beyond the terminal edge, so that the cutting step further comprises opening the plurality of grasper component members from a first closed position to a second open position and then rotating the plurality of grasper component members so that the cutting edge cooperates with the terminal edge of the cutting tube to create the free tissue graft. In certain variations, the cutting may create a free tissue graft that is a core with a hollow center in which the nerve end is at least partially disposed.

The method may include securing or attaching the nerve (e.g., a nerve end or fascicles) to a portion of the free tissue graft either prior to or after the ejecting. For example, the free tissue grafts can be attached to the nerve via sutures, glue, tension, microsutures, physical connectors, manual fixation, autofixation, or other suitable attachment methods or mechanisms. In certain alternative variations, it should be noted that the methods may include introducing at least one electrical conductor into the free tissue graft prior to securing the portion or branch of the nerve to the free tissue graft, or prior to the ejecting. The electrical conductor may be delivered as part of the tool or may be independently introduced. In such a method, the implantable neural graft assembly formed comprises the nerve end and the electrical conductor disposed within the free tissue graft. As discussed above, the at least one electrical conductor provides electrical communication with the nerve of the implanted neural graft assembly.

In certain aspects, the implantable neural graft assembly may thus create stable neuromuscular junctions with the muscle grafts. The muscle reinnervation can treat, mitigate, or prevent the long term development of neuromas, which can be a source of pain and signal interference in a subject. Accordingly, in certain aspects, the present disclosure also contemplates use of such implantable neural interface assemblies for minimizing or preventing formation of neuromas. It is noted that "minimizing" or "mitigating" are intended to mean that the presence of the neural graft assembly implant attached to a nerve ending substantially reduces pain and severity of any symptoms associated with neuromas, while not necessarily completely preventing or inhibiting formation of a neuroma over time. While some disorganized neural growth may still occur over time, the use of an implantable neural graft assembly in accordance with certain aspects of the present disclosure advantageously reduces symptoms and pain as compared to conventional neuroma treatment techniques. Thus, in certain aspects, the present technology provides an implantable neural graft assembly that ultimately results in a lesioned nerve reinnervating the autologous free tissue graft making it quiescent, rather than forming a neuroma. Further, in certain variations, where an electrical conductor is present in the implantable neural graft assembly, it can be used to apply electrical impulses for pain modulation and desensitizing of the nerve ending for additional treatment of neuromas. Thus, the present disclosure contemplates use of such methods and tools to treat neuromas, such as neuromas that occur following amputation, trauma, or Morton's neuromas (occurring in feet).

In certain other aspects, the method may include cutting a portion of a nerve, such as cutting an ending of the nerve, in the subject to create the nerve end (e.g., one or more branches or fascicles) prior to grasping it with the grasper mechanism of the device. In certain aspects, the cutting step may include cutting the nerve ending into a plurality of portions, like branches/fascicles. Thus, the introducing, cutting, grasping and disposing of the nerve in the free tissue graft, optional introducing of the electrical conductor into the free tissue graft assembly, and ejecting steps, may be repeated for each respective portion of the nerve. In certain aspects, a maximum dimension of the free tissue graft is less than or equal to about 10 cm. In other aspects, a maximum dimension of the free tissue graft is less than or equal to about 5 cm.

Because the free tissue grafts, e.g., muscle grafts, may be surgically harvested from non-essential donor muscle within the subject, the free tissue grafts undergo a process of complete deinnervation after being excised and harvested, where previously intact and existing innervation within the free tissue grafts terminates. As discussed above, this cutting process also causes devascularization of the native cells of the free tissue grafts. Once the free tissue grafts are attached to nerve endings via use of the tool and/or methods of the present disclosure, the free tissue grafts undergo a process of reinnervation, where the attached nerve end reinnervates the free tissue grafts and sprouts nerve fibers, which grow within the free tissue grafts in search of new neural targets. Having previously undergone the process of deinnervation, the signals from the newly attached nerve fascicles and newly sprouted nerve fibers do not have to compete with residual nerve signals from the nerve fascicles and nerve fibers that previously innervated the free tissue grafts.

Instead of the tissue dying and being reabsorbed by the subject's body, once implanted and surgically reattached to the subject, the free tissue grafts can acquire nutrients through a process of imbibition. As such, even without a native vascular blood supply, if the implanted free tissue graft is within an optimal volume/size range, the free tissue graft can absorb nutrients and blood through the surrounding tissue and fluids to support the process of reinnervation. Eventually, a new blood supply network may be established as the free tissue graft reintegrates with the subject's body. This process of deinnervation of the free tissue graft followed by reinnervation of the free tissue graft by the attached nerve fascicle through newly sprouted nerve fibers, coupled with the process of imbibition and revascularization, results in an area of muscle or other tissue from which a highly specific electrical signal from an individual nerve fascicle that is greater than or equal to about 250 µV pp or higher, for example, can be received by an implant device, for example.

As mentioned above, to facilitate the processes of reinnervation and imbibition, the free tissue grafts cut from the source of tissue are preferably within an optimal volume/size range. For example, the volume/size of the free tissue graft may be selected to be small enough that it is quickly revascularized by collateral blood flow, while providing a sufficiently sized area or volume for the nerves to grow without forming disorganized neuromas. As noted above, appropriate sizes for such a free tissue graft are significantly greater than a biopsy sample, which are relatively small in dimension and volume and would be of insufficient size for adequate and successful reinnervation in the implantable neural graft assembly.

A greatest dimension of the free tissue graft may be less than or equal to about 10 cm, in certain preferred aspects. For example, in certain variations, the free tissue graft may have a maximum dimension in any direction of less than or equal to about 10 cm. For example, in certain variations, a length of the free tissue graft 10 may be less than or equal to about 10 cm or, more preferably, less than or equal to about 5 cm. Further, a width or diameter of the free tissue graft may be less than or equal to about 10 cm or, more preferably, less than or equal to about 5 cm. The thickness or diameter of the free tissue graft may optionally be less than or equal to about 2 to 3 cm. Further, optimal dimensions for the free tissue graft may include a length of greater than or equal to about 1 cm to less than or equal to about 10 cm, optionally greater than or equal to about 2 cm to less than or equal to about 5 cm, and in certain variations, optionally greater than or equal to about 2 cm to less than or equal to about 4 cm. An optimal diameter of the free tissue graft in certain variations may be greater than or equal to about 0.5 cm to less than or equal to about 5 cm, optionally greater than or equal to about 0.5 cm to less than or equal to about 3 cm, and in certain variations, optionally greater than or equal to about 0.5 cm to less than or equal to about 2 cm. For example, in one variation, optimal dimensions for the free tissue graft may include a length of approximately 3 cm and a diameter of approximately 1 cm.

The dimensions and volume of the internal bore 32 of cutting tube 30 are thus sized to cut a tissue graft having these desired predetermined dimensions. It should be noted that the free tissue graft, and thus cutting tube 30 cross-sectional shape, may have a variety of distinct dimensions and/or geometries and those described herein are exemplary. However, in certain desirable aspects, the free tissue graft formed has a hollow core region.

An exemplary surgical procedure for implanting a neural graft assembly by use of the devices or tools according to the present disclosure is shown in FIGS. 6-14. The tool 20 shown in FIGS. 1-5 is used for illustration. In FIG. 6, the distal end 22 of tool 20 approaches a source of tissue 150 in a subject. The source of tissue 150 may be muscle or dermal tissue. The distal end 22 includes the plurality of grasper component members 40 extending distally beyond the terminal edge 140 of cutting tube 30. The plurality of grasper component members 40 includes the first grasper component 120 and the second grasper component 122, which are in a first closed position (where the angle of opening respectively between them is 0°). Handle 60 is near a lower side 68 of housing 70 and thus arm 63 is in a closed neutral resting position. One or more fingers of a user may be seated in or looped through the finger loop 62 to hold the tool 20 in position.

In FIG. 7, the distal end 22 of tool 20 is advanced into and penetrates the source of tissue 150 to a depth corresponding to the entire length of the cutting tube 30. However, the tissue sample is only collected within a terminal region 151 of the open internal bore 32 of cutting tube 30, which may be delineated by the plunger 54 in a retracted position or by another physical barrier introduced into the internal bore 32. Thus, a front side 152 of housing 70 abuts an exposed surface 154 of the source of tissue 150. Notably, the entire length of the cutting tube 30 need not be advanced into the source of tissue 150 where a desired height of the tissue graft has already been collected in the terminal region 151. In certain variations, the housing could also be tapered to permit a tissue sample to be harvested along a surface of the source of tissue (e.g., collected parallel or at a shallow angle with respect to the surface of the source of tissue). As the terminal edge 140 of cutting tube 30 moves into the source of tissue 150, a core of graft tissue is circumferentially cut and collected within the internal void or bore 32. Notably, because of the presence of the plurality of grasper component members 40, the core of graft tissue collected will be hollow in the center.

In FIG. 8, the handle 60 and thus arm 63 is pushed down and away from the lower side 68 of housing 70 to an open position. Moving the handle 60 to an open position causes the first grasper component 120 to splay or open at an angle with respect to the second grasper component 122. As shown in FIG. 8, the angle is approximately 90° between the first grasper component 120 and the second grasper component 122. Thus, the first grasper component 120 and the second grasper component 122 are moved to a second open position, by pulling the handle 60 down and away from the housing 70. The outer cutting surface 136 of the first grasper component 120 contacts the terminal edge 140 of cutting tube 30 in the second open position.

In FIG. 9, the rotatable wheel 100 at proximal end 26 of tool 20 is turned by the user. The turning of rotatable wheel 100 causes the plurality of grasper component members 40 to rotate at the distal end 22. Thus, turning the rotatable wheel 100 causes the first grasper component 120 to rotate, so that the outer cutting surface 136 contacts the terminal edge 140. As the first grasper component 120 rotates 360°, the outer cutting surface 136 contacts the entire circumference of the terminal edge 140 of cutting tube 30, serving to sever and cut any tissue collected within the open internal bore 32 of the cutting tube 30. Thus, after this cutting step, a free tissue graft 160 is collected within the internal bore 32. The distal end 22 of tool 20 may then be withdrawn and removed from the source of tissue 150. Muscle tissue is quite elastic, thus the first grasper component 120 and the second grasper component 122 may remain in the second open position to ensure that the harvested free tissue graft remains within internal bore 32 of cutting tube 30 as the tool 20 is removed for subsequent steps of the surgical procedure. To keep the first grasper component 120 and the second grasper component 122 in the second open position, pressure may be held on the handle 60 so that it remains open.

In FIG. 10, distal end 22 of tool 20 (having the free tissue graft 160 disposed therein) approaches a nerve 162 in a second surgical location 164. During approach, the first grasper component 120 and the second grasper component 122 may remain in the second open position by retaining pressure on the handle 60 so that it remains open. Once the first grasper component 120 and the second grasper component 122 are located in proximity to nerve 162, the handle 60 can be retracted to a closed resting position where arm 63 is close to the lower side 68 of housing 70, as shown in FIG. 11. The closing of handle 60 in turn causes the first grasper component 120 and the second grasper component 122 to return to the first closed position. The closing of the handle 60 can be done gently to carefully apply the desired amount of compressive force to the nerve 162 without damaging it. In this manner, the first grasper component 120 and the second grasper component 122 grab and retain the nerve 162.

Figure 12:
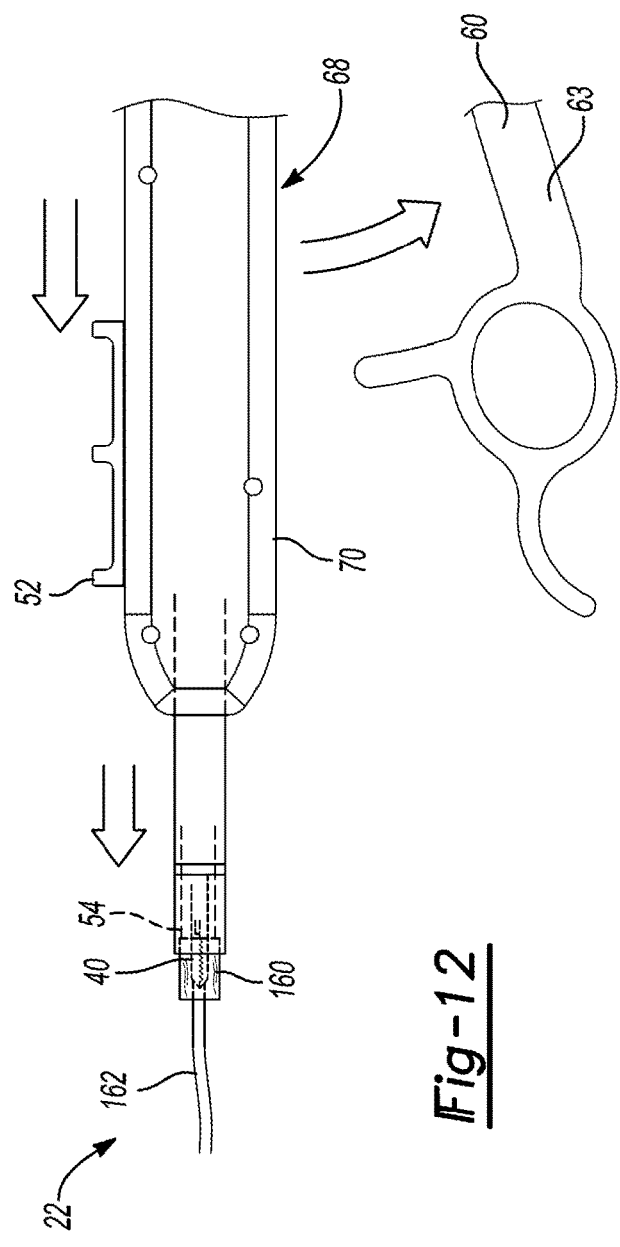
FIG. 12 is a side view of the tool in FIGS. 6-11, where an ejector is deployed to push the tissue core out of the cutting tube, while the peripheral nerve end continues to be grasped by the plurality of grasper component members on the terminal end of the tool.

In FIG. 12, the tissue ejection slide component 52 can be slid forward or distally towards the distal end 22 of the tool 20. By sliding the tissue ejection slide component 52, the entire ejector assembly 50, including plunger 54 is translated distally forward. The tissue ejection slide component 52 will hit a first predetermined stop. While the plurality of grasper component members 40 are laterally fixed with respect to tool 20, the plunger 54 slides laterally forward and then pushes the free tissue graft out over a portion of the nerve 162. In this manner, the tool 20 positions the nerve 162 inside the core of the free tissue graft 160. Then, handle 60 is at least partially opened away from the lower side 68 of housing 70 to at least partially open the plurality of grasper component members 40 and release nerve 162, as shown in FIG. 12.

Figure 13:
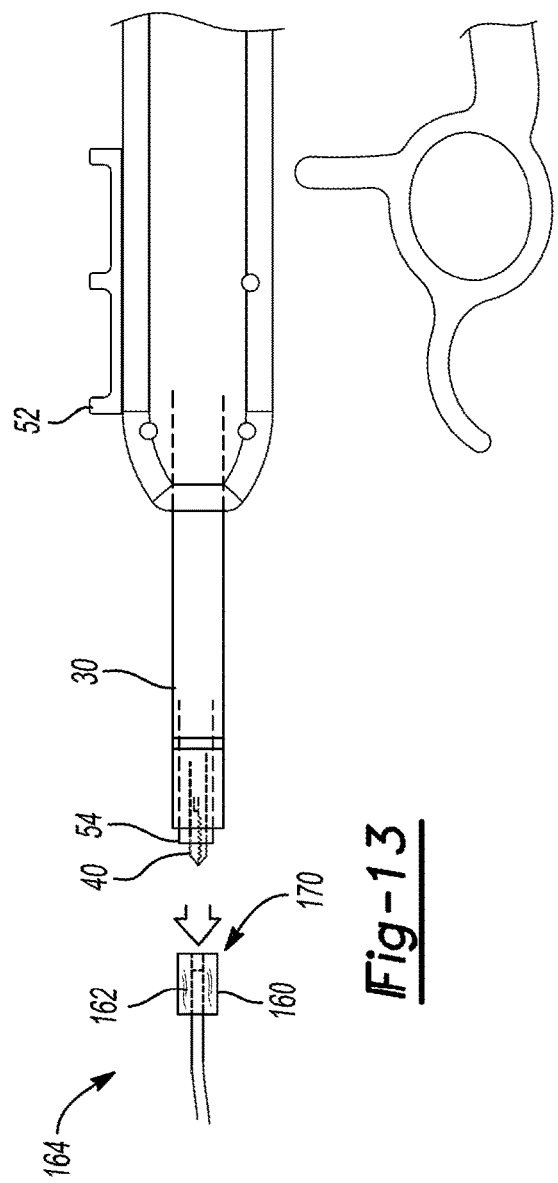
FIG. 13 is a side view of the tool in FIGS. 6-12, where the tissue core has exited the cutting tube and the plurality of grasper component members have released the peripheral nerve end, thus forming an implantable neural graft assembly for the peripheral nerve end.

In FIG. 13, the tissue ejection slide component 52 will hit a second predetermined stop (corresponding to a maximum travel distance of a distal end of the longitudinal slot 56 in housing 70 shown in FIG. 2). In certain variations, a safety lockout can be included that restricts movement of tissue ejection slide component 52 until the plurality of grasper component members 40 has been released to prevent premature or accidental nerve misplacement. Moving the tissue ejection slide component 52 to the second predetermined stop causes a neural graft assembly implant 170 to be ejected from the tool 20 in the second surgical location 164. The neural graft assembly implant 170 includes the end of nerve 162 and the free tissue graft 160 connected together.

Suturing or fixation of nerve 162 can occur after the free tissue graft 160 has been slid over the nerve 162, but before the neural graft assembly implant 170 has been released by the plurality of grasper component members 40 (as shown in FIG. 12). Alternatively, suturing or fixation of nerve 162 to free tissue graft 160 can occur after the neural graft assembly implant 170 is ejected from the tool 20 (as shown in FIG. 13). For example, the suturing or fixation of the nerve 162 to the free tissue graft 160 can be achieved by applying surgical adhesives or glues, such as fibrin glue, cyanoacrylates, and the like, or by manual or automatic fixation techniques, such as sutures, staples, pins, tacks, and the like.

Figure 14:
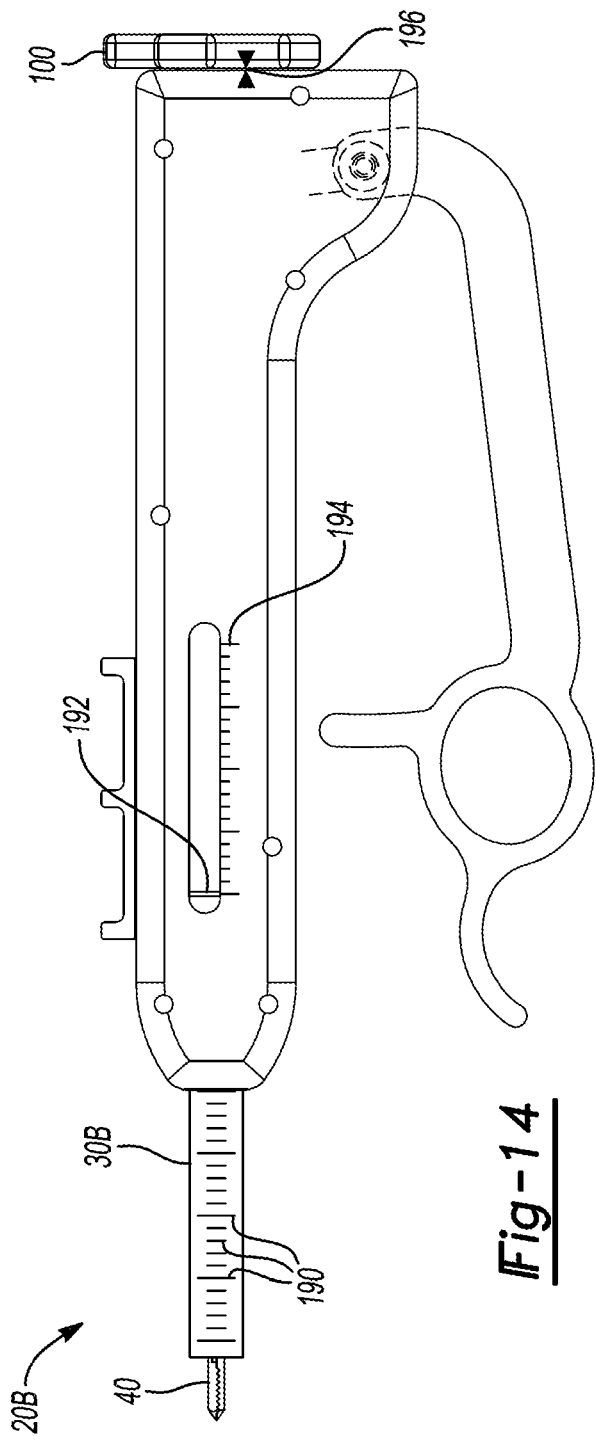
FIG. 14 shows an alternative variation of a medical device tool for creating a peripheral nerve graft interface assembly in a subject in accordance with certain alternative aspects of the present disclosure.

FIG. 14 shows an alternative variation of a medical device or tool 20B for creating a peripheral nerve interface assembly in a subject in accordance with certain alternative aspects of the present disclosure. Where the components are the same as those described in the context of FIGS. 1-5, the same reference numbering will be used and for brevity these components will not be discussed again. Tool 20B has a cutting tube 30B that has optional external indicia, such as first dimensional markings 190, which permit the user to see the depth of insertion of the cutting tube 30B into a source of tissue in the subject. Tool 20B also has an optional gauge 192 arranged with optional second dimensional markings 194. The gauge 192 can indicate either free tissue graft height or nerve position. Thus, first dimensional markings 190 and gauge 192/second dimensional markings 194 may be used exclusively from one another or may be combined together in tool 20B. For example, gauge 192/second dimensional markings 194 on the tool 20B can display to the user the height of the free tissue graft collected and contained within the cutting tube 30B. Alternatively, the height of the free tissue graft could be ascertained by the first dimensional markings 190 on the cutting tube 30B. Further, gauge 192 can show the position of the plurality of grasper component members 40 relative to the end of the free tissue graft (not shown) during the positioning and ejecting processes, so that the depth at which the nerve end will be placed in the free tissue graft can be measured. Tool 20B may also optionally have a third set of markings 196 around the rotatable wheel 100 (either on the exterior of housing 70 or on the rotatable wheel 100 itself), which show a user the amount the rotatable wheel 100 has been turned.

In other aspects, the tool may include a safety device that will restrict movement and limit an amount of force that can be used on the handle 60 as it is clamped down to the first closed position to prevent nerve damage. In other variations, the tool may include an automatic release of the handle 60, as are known in the art, which can be used when the tissue ejection slide component 52 is pushed to eject the neural graft assembly formed by the tool. In yet another aspect, the tool may have a pump-action button, instead of a two-stage ejection slide component 52, where the pump-action button is pushed once to position the nerve inside the free tissue graft core and then the button returns to its initial position for a second push, which serves to eject the neural graft assembly implant (e.g., the muscle-nerve construct). In other aspects, instead of a handle to control the opening and closing of the plurality of the grasper components, the tool may instead have a sliding mechanism for opening the plurality of grasper component members from a first closed position to a second open position. In alternative embodiments, other design variations are likewise contemplated within the tool to achieve the same or similar functions as the components described previously above.

FIGS. 18-23 show another variation of a device or tool 200 for creating an implantable neural graft assembly in a subject in accordance with the present disclosure. Tool 200 has a terminal end 210 with a cutter mechanism including a cutting tube 220 for cutting tissue shown in FIGS. 18-19. The cutting tube 220 includes a first bifurcated portion 222 and a second bifurcated portion 224 at the terminal end 210. The inner second bifurcated portion 224 (having a smaller diameter) is concentrically arranged within the outer first bifurcated portion 222 (having a larger diameter). In this manner, the first bifurcated portion 222 and second bifurcated portion 224 are arranged and aligned as concentric tubes with respect to one another. The first bifurcated portion 222 also defines a first hemispherical portion 226 (notably, the first hemispherical portion 226 may occupy more or less than a hemisphere, but is only a portion of a cylinder or tube). The second bifurcated portion 224 defines a second hemispherical portion 228 (the second hemispherical portion 228 likewise may occupy more or less than a hemisphere, but is only a portion of a cylinder or tube). In a first position, the first hemispherical portion 226 and the second hemispherical portion 228 are nested within and against one another. Thus, in the first position (shown in FIGS. 18 and 20), the terminal end 210 only has a low profile hemispherical shape.

However, in tool 200, either the first bifurcated portion 222 or the second bifurcated portion 224 rotates with respect to the other of the first bifurcated portion 222 or the second bifurcated portion 224. In the design shown in FIGS. 18-23, the first bifurcated portion 222 rotates, while the second bifurcated portion 224 remains stationary. In certain variations, the first bifurcated portion 222 is capable of rotating by at least 180° to a second position (shown in FIGS. 19 and 21). In the second position, the first hemispherical portion 226 and the second hemispherical portion 228 are complementary and together create a cylinder or tube structure occupying at least 360°. Thus, in the second position, the inserted cutting tube 220 has an open central region that can receive tissue captured via the insertion and rotation process. Lateral edges 230 of the first hemispherical portion 226 overlap with lateral edges 232 of the second hemispherical portion 228.

As shown in FIGS. 20-21, the terminal end 210 of tool 200 may be advanced into a source of tissue 246 of a subject from which a free tissue graft is to be harvested. As shown in FIG. 20, the terminal end 210 is introduced into the source of tissue 246 in the first position where the first hemispherical portion 226 and the second hemispherical portion 228 are nested within and against one another. After introduction into the source of tissue 246, first hemispherical portion 226 is rotates 180° to the second position (as shown in FIG. 21). The insertion of the stationary second hemispherical portion 228 followed by opening via rotation of the first hemispherical portion 226 thus circumferentially cuts tissue to create a cylindrical free tissue graft 250. In certain variations, the tool 200 may also have the ability to further rotate the terminal end 210 (e.g., 360°) for additional cutting, as described above.

A body portion 234 of tool 200 includes a hollow center core 236 that receives a grasper assembly 240 of a grasper mechanism (shown in FIGS. 18-19 and 22-23). The body portion 234 further includes a housing 238. The grasper assembly 240 includes a plurality of grasper component members 242 that is similar to the plurality of grasper component members 40 shown in FIGS. 9-11, which for brevity will not be repeated herein unless otherwise noteworthy. The grasper component members 242 may cooperate with a terminal edge 244, so that rotation of the grasper component members 242 in an open splayed position will create a circumferential cut along the first hemispherical portion 226 and the second hemispherical portion 228 of cutting tube 220 that serves to cut and free the end of the cylindrical free tissue graft 250 having a hollow core contained in the terminal end 210 of tool 200.

After introduction into another surgical site within the patient, the grasper component members 242 of grasper assembly 240 can be opened to receive and closed to retain a terminal end of a nerve 252 (shown in FIGS. 22-23). Then, cylindrical free tissue graft 250 may be distally moved or ejected from the terminal end 210 of tool 200 over the nerve 252 being retained in the grasper component members 242, as shown in FIG. 23. Such an ejection of the free tissue graft 250 may be accomplished by an ejector assembly like those described above that may include a plunger. It should be noted that the nerve 252 may also be pulled into the core of the free tissue graft 250, in which case, any need for an ejector assembly would be eliminated. After the free tissue graft 250 is disposed over the nerve end 252, the implanted nerve graft assembly may be left within the subject.

FIGS. 24-27 show another variation of a device or tool 300 for creating an implantable neural graft assembly in a subject in accordance with the present disclosure. Tool 300 has a cutter mechanism in the form of a box plane cutter 310 (e.g., a mandoline) box planer. The box plane cutter 310 includes an opening or slit 312. A cutting blade 314 is disposed within the slit 312 and protrudes from a lower surface 316 of the box plane cutter 310. In this manner, the box plane cutter 310 of tool 300 can be moved along an exposed surface 318 of a source of tissue 320 in a subject in the direction indicated in FIG. 24. As the box plane cutter 310 moves against the exposed surface 318 (in a direction parallel to the exposed surface), applied pressure presses the cutting blade 314 into the source of tissue 320 and shears and removes a strip of tissue graft 322. Notably, a reverse configuration that is not shown is also contemplated, where the box plane cutter may have the blade on the opposite side of the slit and thus be pulled towards the surgeon or user to create the strip of tissue graft. The strip of tissue graft 322 thus may have a planar shape (e.g., rectangular, as best shown in FIG. 25) and may be cut to the appropriate predetermined size. A thickness of the strip of tissue graft 322 may be controlled by the cutting blade 314 depth and the dimensions of the slit 312.

Thus, FIG. 25 shows the planar strip of tissue graft 322 harvested from the source of tissue 320 in FIG. 25. The strip of tissue graft 322 can be cut to the desired dimensions after being harvested from the source of tissue 320, as necessary. As shown in FIG. 25, a terminal end of a nerve 330 can be disposed onto the tissue graft 322 within a different surgical site of the subject. The strip of tissue graft 322 can be rolled onto itself (for example, by manual manipulation of a surgeon or clinician), so that a terminal edge 324 folds against a surface 326 of the tissue graft 322. Then, one or more connectors 332 may be used to affix or secure the terminal edge 324 against surface 326 to define a cylindrical tissue graft 334 having a portion of the terminal end of nerve 330 disposed therein. The connector(s) 332 may be any of those discussed previously above, including adhesive, glue, or physical fixation techniques. As shown in FIG. 28, the connectors 332 are staples. While not shown, the end of nerve 330 may also be secured within the cylindrical tissue graft by a connector, as previously discussed above. An implanted cylindrical nerve graft assembly 338 is thus formed (in FIG. 28) that has the cylindrical tissue graft 334 secured by a plurality of connectors 332 with the end of the nerve 330 disposed therein.

FIGS. 26-27 show an additional templating tool 340 that may be used in conjunction with a tissue graft 322 harvested with a box plane cutter 310 design of tool 300. After harvesting with tool 300 and cutting to the desired dimensions, a strip of tissue graft 322 can be placed within the templating tool 340 to assist with formation of the cylindrical tissue graft 334. Tissue graft 322 can be cut to fit within the templating tool 340. Templating tool 340 has two distinct clamshell portions 342 connected at a joint 346 (e.g., hinges or a flexible material). Each clamshell portion 342 defines a curved interior region 349 and a flat lateral lip or edge 350. When the two clamshell portions 342 are in an open position as shown in FIG. 26, the strip of tissue graft 322 can be placed against an interior surface 348, extending along the curved interior region 349 and to the flat lateral edges 350.

In FIG. 27, the clamshell portions 342 are closed to bring lateral edges 350 together. In this manner, the tissue graft 322 comes into contact with itself between the lateral edges 350. The lateral edges 350 further may define a plurality of openings or slots 352 through which one or more connectors 332 (e.g., sutures) may be introduced to the tissue graft 322. In certain other variations, the lateral edges 350 may instead have one or more injection points for introducing glue or adhesive to the tissue graft 322 to affix its edges and form the cylindrical tissue graft 334 structure having a hollow core region 354. While not shown, the lateral edges 350 may further include snaps or other physical securing members to ensure that the clamshell portions 342 remain in a closed position during introduction of the one or more connectors.

The end of nerve 330 may be disposed within the hollow core region 354 of cylindrical tissue graft 334 after closing the clamshell portions 342, although before or after the connector(s) 332 are applied. In other variations, the end of the nerve 330 may be placed in contact with the strip of tissue graft 322 disposed along the interior surface 348 of the clamshell portions 342 prior to closing them. The end of the nerve 330 may be secured to the tissue graft 322 prior to closing the clamshell portions 342 (for example as shown in FIG. 26) or alternatively afterwards (including after the connector(s) 332 are introduced to the graft 322).

FIGS. 29-34 show another variation of a device or tool 400 for creating an implantable neural graft assembly in a subject in accordance with the present disclosure. Tool 400 has a terminal end 410 with a cutter mechanism assembly 420 including a first cutting tube 422 for receiving cut tissue from a subject to create a free graft. The cutter mechanism assembly 420 includes an outer sleeve 430 having a bendable arm tubular component 426 surrounding the cutting tube 422. The outer sleeve 430 having the bendable arm tubular component 424 is capable of linearly translating from a first retracted position (shown in FIGS. 30-31) to a second distally extended position (shown in FIGS. 32 and 34). The bendable arm tubular component 424 is also capable of rotating at least 360°. The bendable arm tubular component 424 has a sharpened arm 426 that is capable of being inwardly angled or bent in the second distally extended position.

The sharpened arm 426 has at least one sharp terminal cutting edge 442. The tool 400 further includes a grasper mechanism assembly 440 with a plurality of grasper component members 450 operable in a similar manner to the previous embodiments discussed previously above. As best seen in FIG. 33, the outer sleeve 430 of cutter mechanism assembly 420 slides over and rotates around the cutting tube 422, as well as over the grasper mechanism assembly 440. The sharp terminal cutting edge 442 on the sharpened arm 426 extends distally beyond the grasper components 450.

In FIG. 30, the terminal end 410 of tool 400 may be advanced into a source of tissue 452 of a subject from which a free tissue graft is to be harvested. As shown in FIG. 30, the terminal end 410 is introduced into the source of tissue 452 when the bendable arm tubular component 424 and sharpened arm 426 is in a first retracted position. After the terminal end 410 is plunged into the source of tissue 452 (shown in FIG. 31), the bendable arm tubular component 424 can be advanced or slid forward (in a distal direction indicated by the arrow in FIG. 32) to its second distally extended position. The sharpened arm 426 thus advances beyond the grasper components 450 and a terminal edge 454 of cutting tube 422. The sharpened arm 426 is bendable (e.g., having a preformed angled bend) and thus extends radially inward in the second distally extended position. A gap 456 is created between the grasper components 450 and an inner surface 458 of sharpened arm 426 in the second distally extended position. In certain variations, the inner surface 458 of sharpened arm 426 may be contacted with the terminal end of grasper components 450 to further ensure cutting of tissue or a gap 456 may be maintained between the terminal end of grasper components 450 and the inner surface 458 of sharpened arm 426.

Next, the outer sleeve 430 of cutter mechanism assembly 420 is advanced forward. The outer sleeve 430 thus extends beyond the cutting tube 422 and the grasper mechanism assembly 440. The sharp terminal cutting edge 442 of sharpened arm 426 extends distally beyond the grasper components 450. Sharpened arm 426 is rotated (e.g., 360°) to cut the tissue. In this manner, a cylindrical free tissue graft 460 having a hollow core is cut and freed from the source of tissue 452. The tool 400 may then be withdrawn from the source of tissue 452 while the bendable arm tubular component 424 and sharpened arm 426 remain in the second distally extended position, retaining the cylindrical free tissue graft 460 as the tool 400 is removed. While not shown, the grasper mechanism assembly 440 including grasper components 450 can be used to implant the cylindrical free tissue graft 460 around a peripheral nerve end in the subject to form a neural graft assembly, as described previously above.

FIGS. 35-41 show another variation of a device or tool 500 for creating an implantable neural graft assembly in a subject in accordance with the present disclosure. Tool 500 has a terminal end 510 with a cutter mechanism including a clamping cutting tube 520 for cutting tissue to create an implantable graft. Tool 500 has a first hinged cutter portion 522 and a second hinged cutter portion 524 that define two distinct clamshell shaped members. The first hinged cutter portion 522 defines a first cutting edge 526 extending along three sides and a first connecting edge 528. The second hinged cutter portion 524 defines a second cutting edge 530 extending along three sides and a second connecting edge 532. The first hinged cutter portion 522 and the second hinged cutter portion 524 are connected along a joint 540 (e.g., two hinges). Each hinged cutter portion 522, 524 defines a curved interior region 542. The first hinged cutter portion 522 and the second hinged cutter portion 524 are in an open position as shown in FIG. 35 and in a closed position in FIG. 36. In the closed position, the first cutting edge 526 and the second cutting edge 530 are in contact with one another.

The clamping cutting tube 520 further includes a first aperture 544 partially formed in both the first connecting edge 528 of the first hinged cutter portion 522 and the second connecting edge 532 of the second hinged cutter portion 524. The clamping cutting tube 520 also includes a second aperture 546 partially formed in both the first hinged cutter portion 522 and the second hinged cutter portion 524 opposite to the first aperture 544. The first aperture 544 and the second aperture 546 are aligned and cooperate to receive a grasper mechanism assembly 550. The grasper mechanism assembly 550 including a grasper tube 548 is contained within a longitudinal body 552 of tool 500 that defines a major axis "A" that is generally orthogonal to a major axis "B" formed by a major axis of clamping cutting tube 520. Thus, the grasper mechanism assembly 550, including the grasper tube 548, translates along the major axis A and is received within the first aperture 544 and second aperture 546.

As shown in FIG. 37, the terminal end 510 of tool 500 may be advanced into a source of tissue 556 of a subject from which a free tissue graft is to be harvested. As shown in FIG. 37, the first hinged cutter portion 522 and the second hinged cutter portion 524 are in an open position as the tool 500 is brought into contact with the source of tissue 556. The first hinged cutter portion 522 and the second hinged cutter portion 524 are then clamped into a closed position in FIG. 38, where the first cutting edges 526 and second cutting edges 530 cut tissue from the source of tissue 556. A cylindrical free tissue graft 260 is thus captured and retained within the clamping cutting tube 520 as the tool 500 is withdrawn from the surgical site of the subject.

In FIG. 39, the tool 500 is introduced into another surgical site within the subject or patient where the neural graft assembly is to be implanted. The grasper mechanism assembly 550 is linearly translated along the major axis A through the first aperture first aperture 544 through the cylindrical free tissue graft 560 and out through the second aperture 546. The grasper mechanism assembly 550 includes a plurality of grasper component members 562 similar to the designs previously described above, which will not be repeated herein in detail for brevity. Briefly, the grasper component members 562 of grasper assembly 550 can be opened to receive and closed to retain a terminal end of a nerve 570 (generally shown in FIGS. 39-41).

Then, the nerve 570 can be pulled in a proximal direction into a central region of the cylindrical free tissue graft 560 while being retained in the grasper component members 562, as shown in FIG. 40. As in the other embodiments described previously, the nerve 570 may be affixed to the cylindrical free tissue graft 560 via a connector (e.g., adhesive, glue, sutures, and the like). Then, the grasper component members 562 can be slightly opened to release terminal end of nerve 570. The first hinged cutter portion 522 and the second hinged cutter portion 524 are opened to the open position to release and eject an implantable neural graft assembly 572 in the subject that includes a portion of the nerve 570 and the cylindrical free tissue graft 560.

In other variations, the grasper component members 562 retaining the terminal end of nerve 570 and grasper assembly 550 can remain stationary, while the first hinged cutter portion 522 and the second hinged cutter portion 524 of the clamping cutting tube 520 may be moved by sliding motion over the stationary grasper component members 562. The cylindrical free tissue graft 560 is then moved into position over the stationary nerve 570, which can be affixed together as described above. Then, the grasper component members 562 can be opened to release terminal end of nerve 570. Next, the first hinged cutter portion 522 and the second hinged cutter portion 524 may be opened to the open position to release and eject an implantable neural graft assembly 572 in the subject, as described above.

In certain other aspects, the present disclosure provides a kit for forming an implantable neural graft assembly. In certain variations, the implantation kit may include a tool having a cutting mechanism and a grasper component. The cutter component is used for cutting and removing a tissue graft from a source of tissue in the subject to form a cylindrical tissue graft. The grasper component is capable of retaining a nerve end of the subject within the cylindrical tissue graft. In certain aspects, the cutter component may be releasably received within the device or tool. The cutter component may be received within a cutter mechanism of a tool. Thus, certain cutter components may be interchangeable, disposable, and/or replaceable. Where the cutter component is interchangeable, it may be selected from for a variety of distinctly sized cutter components. Thus, the kit may include a plurality of distinctly sized cutter components (e.g., having a cutting tube with distinct diameters or volumes) from which the surgeon or user of the kit may choose. The cutter component is optionally a cutting tube or a box plane cutter, by way of example, although other cutter components discussed previously may be included in the kit. Notably, such a kit may include a device or tool or instead the device or tool may be omitted (e.g., if previously purchased).

In other variations, the grasper component may also likewise be releasably received within the grasper mechanism of a tool. Grasper components may be interchangeable, disposable, and/or replaceable. Where the grasper component is interchangeable, it may be selected from for a variety of distinctly sized or different types of grasper components. Thus, the kit may include a plurality of distinct grasper components (e.g., having grasper components with differently sized grasper members or different types of grasper members) from which the surgeon or user of the kit may choose. The grasper component may be selected from a plurality of grasper component members that cooperate to retain the nerve end, a suction or vacuum tube, a compliant grasper component, a loop grasper, and combinations thereof.

In certain variations, the kit for creating an implantable neural graft assembly in a subject may include, a cutter component, a grasper component, and at least one connector (e.g., an adhering component) for affixing a portion of the nerve end within the cylindrical tissue graft for forming the implantable neural graft assembly comprising the nerve end disposed and affixed within the free tissue graft. The connector may be selected from the group consisting of: adhesive, glue, sutures, staples, tacks, pins, and combinations thereof. Such a kit may further include a tool or the tool may be separately provided.

In certain variations, the kit for creating an implantable neural graft assembly in a subject may include, a cutter component, a grasper component, a templating device, and at least one connector (e.g., an adhering component) for affixing a portion of the nerve end within the cylindrical tissue graft for forming the implantable neural graft assembly comprising the nerve end disposed and affixed within the free tissue graft. The connector may be selected from the group consisting of: adhesive, glue, sutures, staples, tacks, pins, and combinations thereof. Such a kit may optionally further include a tool that receives the cutter component and the grasper component.

In one variation, the kit includes a box plane cutter (e.g., a mandolin style cutter) as the cutter component, so the kit may further include a templating device for creating the cylindrical tissue graft with the at least one connector in the kit. Such an exemplary templating device was described above in the context of FIGS. 26-27. The kit may also include a grasper component and at least one connector.

Thus, the present disclosure provides a simple, mechanically actuated hand-held surgical tool. The tool enables fixation of one biological tissue within another biological tissue. More specifically, the tool provides the ability to create a free tissue graft having a hollow core and pulling and securing a biological material or structure into and within a portion of the hollow core. In certain aspects, the tool is capable of a) cleanly cutting or resecting a predetermined volume of tissue, such as skeletal muscle tissue, to form a free tissue graft b) disposing the free tissue graft around a distal portion of a divided peripheral nerve or other similar structure, c) securing the nerve or similar structure within the free tissue graft, and/or d) releasing the completed regenerative neuromuscular construct as a neural graft assembly implant. Such a tool allows surgeons to quickly and uniformly prepare multiple regenerative neuromuscular constructs (RNCs) for treatment of neuromas or other similar procedures. Creating small skeletal muscle constructs and coaptation of these constructs to the end of the nerve has conventionally required substantial time and surgical skill to perform manually using currently available surgical tools. However, the devices of the present disclosure will enable the surgical procedure to be conducted in far less time, for example, reducing the time of the procedure so that it only lasts about 10 minutes to about 30 minutes per nerve ending.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A device for creating an implantable neural graft assembly in a subject, comprising:
   a cutter mechanism for cutting and removing a tissue graft having a hollow central region from a source of tissue in the subject comprising a cutting tube having an internal bore that cuts the tissue graft from the source of tissue in the subject;
   a grasper mechanism, seating within the internal bore of the cutting tube, comprising at least one grasping surface capable of retaining a nerve end of the subject in a first position and releasing the nerve end in a second position, wherein the at least one grasping surface is treated, patterned, or formed of a material that enhances friction forces and retention of the nerve end when the grasper mechanism is in the first position, wherein the grasper mechanism comprises a plurality of grasper component members that is rotatable greater than or equal to about 360°, wherein the first position is a first closed position that retains the nerve end and the second position is a second open position that releases the nerve end, and the device further comprises a handle that moves the plurality of grasper component members from the first closed position to the second open position and a controller component that rotates the plurality of grasper component members, wherein at least one of the plurality of grasper component members has a cutting edge that cooperates with a terminal end of the cutting tube to create the tissue graft contained in the internal bore; and an actuation mechanism configured to eject and dispose the tissue graft over the nerve end, wherein the device creates the implantable neural graft assembly comprising the nerve end disposed within the tissue graft.

2. The device of claim 1, wherein the cutting edge of the at least one grasper component member is sharpened to have a cutting angle of greater than or equal to about 15° to less than or equal to about 30° and/or a terminal edge of the cutting tube is sharpened to have a cutting angle of greater than or equal to about 15° to less than or equal to about 30°.

3. The device of claim 1, wherein the grasper mechanism further comprises a grasper assembly connected to the plurality of grasper component members, wherein the grasper assembly is at least partially disposed within the internal bore, wherein the handle is connected to the grasper assembly via a cam and follower assembly to move the plurality of grasper component members from the first closed position to the second open position and the controller component comprises a rotatable wheel connected to the grasper assembly to rotate the plurality of grasper component members.

4. The device of claim 3, wherein the grasper assembly comprises a cylindrical member connected to the plurality of grasper component members that is centrally disposed within the internal bore of the cutting tube and an ejector mechanism comprising a plunger for ejecting the tissue graft, wherein the ejector mechanism is disposed concentrically about and linearly translates with respect to the cylindrical member, wherein the hollow central region is formed by the presence of the cylindrical member in the internal bore.

5. The device of claim 1, wherein the cutter mechanism further comprises a bendable sharpened arm surrounding the cutting tube that linearly translates from a first retracted position to a second extended position, wherein in the second extended position the bendable sharpened arm is rotatable to greater than or equal to about 360° to cut and remove the tissue graft.

6. The device of claim 1, wherein the internal bore of the cutting tube is dimensioned to cut the tissue graft to have a length of greater than or equal to about 1 centimeters to less than or equal to about 10 centimeters and a diameter or width of greater than or equal to about 0.5 centimeters to less than or equal to about 5 centimeters.

7. The device of claim 1 wherein the actuation mechanism further comprises a plunger connected to a tissue ejection slide component that linearly translates the plunger.

8. The device of claim 1, wherein the cutter mechanism comprises a clamping cutting tube having two hinged portions each defining a cutting edge that engages with the other cutting edge, wherein the clamping cutting tube defines a first aperture and a second aperture opposite to the first aperture, wherein the first aperture and the second aperture receive a portion of the grasper mechanism.

9. The device of claim 1, wherein the cutter mechanism comprises a cutter component that is releasably received within the device and the grasper mechanism comprises a grasper component that is also releasably received within the device.

10. The device of claim 1, wherein the at least one grasping surface is patterned and comprises at least one of corrugations or serrations.

11. The device of claim 10, wherein the at least one grasping surface comprises a first grasping surface comprising serrations on a first grasper component member of the plurality of grasper component members and a second grasping surface comprising serrations on a second grasper component member of the plurality of grasper component members, wherein the serrations on the first grasping surface and the serrations on the second grasping surface together define an interlocking saw tooth pattern in the first position.

12. The device of claim 1, wherein the at least one grasping surface is treated with a surface treatment selected from the group consisting of: an etched surface, a roughened surface, and a non-slip coating.

13. The device of claim 1, wherein the at least one grasping surface comprises a compliant foam material.

14. A method of forming an implantable neural graft assembly in a subject, the method comprising:

introducing a device into a source of tissue in the subject comprising a cutter mechanism comprising a cutting tube having an internal bore that cuts and removes a tissue graft from the source of tissue in the subject, a grasper mechanism seated within the internal bore of the cutting tube, comprising at least one grasping surface capable of retaining a nerve end of the subject in a first position and releasing the nerve end in a second position, wherein the grasper mechanism comprises at least one grasping surface that is treated, patterned, or formed of a material that enhances friction forces and retention of the nerve end of the subject in the first position and releasing the nerve end in the second position, and the grasper mechanism further comprises a plurality of grasper component members that are rotatable greater than or equal to about 360°, wherein the device further comprises a handle that moves the plurality of grasper component members from a first closed position to a second open position and a controller component that rotates the plurality of grasper component members, wherein at least one of the plurality of grasper component members has a cutting edge that cooperates with a terminal end of the cutting tube to create the tissue graft contained in the internal bore, and an actuation mechanism configured to eject and dispose the tissue graft over the nerve end;

cutting a free tissue graft from the source of tissue with the cutter mechanism, wherein the free tissue graft is retained in the cutter mechanism as the device is removed from the source of tissue;

grasping the nerve end with the at least one grasping surface of the grasper mechanism and introducing it into a portion of the free tissue graft; and ejecting the free tissue graft with the actuation mechanism from the device to create the implantable neural graft assembly comprising the nerve end disposed within the free tissue graft.

15. The method of claim 14, wherein the plurality of grasper component members extends beyond the terminal end, so that the cutting further comprises opening the plurality of grasper component members from the first closed position to the second open position and then rotating the plurality of grasper component members so that the cutting edge cooperates with the terminal end of the cutting tube to create the free tissue graft.

16. The method of claim 14, further comprising affixing the nerve end to a portion of the free tissue graft either prior to or after the ejecting.

17. The method of claim 14, further comprising introducing an electrical conductor into the free tissue graft prior to the ejecting, wherein the implantable neural graft assembly comprises the nerve end and the electrical conductor disposed within the free tissue graft.

18. A device for creating an implantable neural graft assembly in a subject, comprising:
   a cutter mechanism for cutting and removing a tissue graft having a hollow central region from a source of tissue in the subject comprising a cutting tube having an internal bore that cuts the tissue graft from the source of tissue in the subject;
   a grasper mechanism capable of retaining a nerve end of the subject in a first position and releasing the nerve end in a second position and wherein the grasper mechanism is seated within the internal bore of the cutting tube and the grasper mechanism comprises a plurality of grasper component members that is rotatable greater than or equal to about 360°, wherein the first position is a first closed position that retains the nerve end and the second position is a second open position that releases the nerve end, and the device further comprises a handle that moves the plurality of grasper component members from the first closed position to the second open position and a controller component that rotates the plurality of grasper component members, wherein at least one of the plurality of grasper component members has a cutting edge that cooperates with a terminal end of the cutting tube to create the tissue graft contained in the internal bore, wherein the cutting edge of the at least one grasper component member is sharpened to have a cutting angle of greater than or equal to about 15° to less than or equal to about 30° and/or a terminal edge of the cutting tube is sharpened to have a cutting angle of greater than or equal to about 15° to less than or equal to about 30° and the cutting edge of the at least one grasper component member has a recessed region in which the terminal edge of the cutting tube seats; and
   an actuation mechanism configured to dispose the tissue graft over the nerve end, wherein the device creates the implantable neural graft assembly comprising the nerve end disposed within the tissue graft.

19. The device of claim 18, wherein the first position is a first closed position that retains the nerve end and the second position is a second open position that releases the nerve end and the handle is connected to the grasper mechanism via a cam and follower assembly to move the plurality of grasper component members from the first closed position to the second open position and the controller component comprises a rotatable wheel connected to the grasper mechanism to rotate the plurality of grasper component members.

20. The device of claim 19, wherein the grasper mechanism comprises a cylindrical member connected to the plurality of grasper component members that is centrally disposed within the internal bore of the cutting tube and an ejector mechanism comprising a plunger for ejecting the tissue graft, wherein the ejector mechanism is disposed concentrically about and linearly translates with respect to the cylindrical member, wherein the hollow central region is formed by the presence of the cylindrical member in the internal bore.

21. The device of claim 18, wherein the cutter mechanism further comprises a bendable sharpened arm surrounding the cutting tube that linearly translates from a first retracted position to a second extended position, wherein in the second extended position the bendable sharpened arm is rotatable to greater than or equal to about 360° to cut and remove the tissue graft.

22. The device of claim 18, wherein the internal bore of the cutting tube is dimensioned to cut the tissue graft to have a length of greater than or equal to about 1 centimeter to less than or equal to about 10 centimeters and a diameter or width of greater than or equal to about 0.5 centimeters to less than or equal to about 5 centimeters.

23. The device of claim 18, wherein the actuation mechanism further comprises a plunger connected to a tissue ejection slide component that linearly translates the plunger.

24. The device of claim 18, wherein the cutter mechanism comprises a clamping cutting tube having two hinged portions each defining a cutting edge that engages with the other cutting edge, wherein the clamping cutting tube defines a first aperture and a second aperture opposite to the first aperture, wherein the first aperture and the second aperture receive a portion of the grasper mechanism.

25. The device of claim 18, wherein the cutter mechanism comprises a cutter component that is releasably received within the device and the grasper mechanism comprises a grasper component that is also releasably received within the device.

26. A device for creating an implantable neural graft assembly in a subject, comprising:
   a cutter mechanism for cutting and removing a tissue graft having a hollow central region from a source of tissue in the subject comprising a cutting tube having an internal bore that cuts the tissue graft from the source of tissue in the subject, wherein the cutting tube comprises a first bifurcated portion and a second bifurcated portion concentrically disposed around the first bifurcated portion, the second bifurcated portion is rotatable to greater than or equal to about 180° and cooperates with the first bifurcated portion to cut and remove the tissue;
   a grasper mechanism capable of retaining a nerve end of the subject in a first position and releasing the nerve end in a second position, wherein the grasper mechanism is seated within the internal bore of the cutting tube; and
   an actuation mechanism configured to dispose the tissue graft over the nerve end, wherein the device creates the implantable neural graft assembly comprising the nerve end disposed within the tissue graft.

27. The device of claim 26, wherein the grasper mechanism comprises a grasper component selected from the group consisting of: a plurality of grasper component members that cooperate to retain the nerve end in the first position, a suction tube, a compliant grasper component, and a loop grasper.

28. The device of claim 26, wherein the grasper mechanism comprises a plurality of grasper component members that is rotatable greater than or equal to about 360°, wherein the first position is a first closed position that retains the nerve end and the second position is a second open position that releases the nerve end, and the device further comprises a handle that moves the plurality of grasper component members from the first closed position to the second open position and a controller component that rotates the plurality of grasper component members, wherein at least one of the plurality of grasper component members has a cutting edge that cooperates with a terminal end of the cutting tube to create the tissue graft contained in the internal bore.

29. The device of claim 28, wherein the cutting edge of the at least one of the plurality of grasper component members is sharpened to have a cutting angle of greater than or equal to about 15° to less than or equal to about 30° and/or a terminal edge of the cutting tube is sharpened to have a cutting angle of greater than or equal to about 15° to less than or equal to about 30°.

30. The device of claim 28, wherein the grasper mechanism further comprises a grasper assembly connected to the plurality of grasper component members, wherein the grasper assembly is at least partially disposed within the internal bore, wherein the handle is connected to the grasper assembly via a cam and follower assembly to move the plurality of grasper component members from the first closed position to the second open position and the controller component comprises a rotatable wheel connected to the grasper assembly to rotate the plurality of grasper component members.

31. The device of claim 30, wherein the grasper assembly comprises a cylindrical member connected to the plurality of grasper component members that is centrally disposed within the internal bore of the cutting tube and an ejector mechanism comprising a plunger for ejecting the tissue graft, wherein the ejector mechanism is disposed concentrically about and linearly translates with respect to the cylindrical member, wherein the hollow central region is formed by the presence of the cylindrical member in the internal bore.

32. The device of claim 26, wherein the internal bore of the cutting tube is dimensioned to cut the tissue graft to have a length of greater than or equal to about 1 centimeter to less than or equal to about 10 centimeters and a diameter or width of greater than or equal to about 0.5 centimeters to less than or equal to about 5 centimeters.

33. The device of claim 26, wherein the actuation mechanism further comprises a plunger connected to a tissue ejection slide component that linearly translates the plunger.

34. The device of claim 26, wherein the grasper mechanism comprises at least one grasping surface capable of retaining the nerve end in the first position and releasing the nerve end in the second position, wherein the at least one grasping surface is treated, patterned, or formed of a material that enhances friction forces and retention of the nerve end when the grasper mechanism is in the first position.

35. The device of claim 34, wherein the at least one grasping surface is patterned and comprises at least one of corrugations or serrations.

36. The device of claim 35, wherein the grasper mechanism comprises a plurality of grasper component members that cooperate to retain the nerve end in the first position, wherein the at least one grasping surface comprises a first grasping surface comprising serrations on a first grasper component member of the plurality of grasper component members and a second grasping surface comprising serrations on a second grasper component member of the plurality of grasper component members, wherein the serrations on the first grasping surface and the serrations on the second grasping surface together define an interlocking saw tooth pattern in the first position.

37. The device of claim 34, wherein the at least one grasping surface is treated with a surface treatment selected from the group consisting of: an etched surface, a roughened surface, and a non-slip coating.

38. The device of claim 34, wherein the at least one grasping surface comprises a compliant foam material.

* * * * *